US006242415B1

(12) United States Patent
Mohagheghpour

(10) Patent No.: US 6,242,415 B1
(45) Date of Patent: Jun. 5, 2001

(54) MEDIATION OF CYTOKINES BY MELANIN

(75) Inventor: Nahid Mohagheghpour, San Francisco, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 08/798,846

(22) Filed: Feb. 12, 1997

(51) Int. Cl.[7] ................................................. A61K 38/00
(52) U.S. Cl. ..................................................................... 514/2
(58) Field of Search ................................................... 514/21

(56) References Cited

U.S. PATENT DOCUMENTS

| 3,987,202 | 10/1976 | Okun | 424/331 |
|---|---|---|---|
| 5,057,325 | * 10/1991 | Montefiori | 424/522 |
| 5,210,076 | * 5/1993 | Berliner et al. | 514/21 |
| 5,340,734 | 8/1994 | della-Cioppa et al. | 435/212 |
| 5,466,592 | 11/1995 | della-Cioppa et al. | 435/212 |
| 5,486,351 | 1/1996 | della-Cioppa et al. | 424/59 |

OTHER PUBLICATIONS

Aderka et al., "Increased Serum Levels of Soluble Receptors for Tumor Necrosis Factor in Cancer Patients," *Cancer Res.* 51:5602–5607 (1991).
Akira, S. and Kishimoto, T. "IL–6 and NF–IL6 in Acute–Phase Response and Viral Infection," *Immunol. Rev.* 127:25–50 (1992).
Ashkenazi et al., "Protection Against Endotoxic Shock by an Tumor Necrosis Factor Receptor Immunoadhesin," *Proc. Natl. Acad. Sci. USA* 88:10535–10539 (1991).
Bagby et al., "Divergent Efficacy of Antibody to Tumor Necrosis Factor–α in Intravascular and Peritonitis Models of Sepsis," *J. Infect. Dis.* 163:83–88 (1991).
Baracos et al., "Stimulation of muscle protein Degradation and prostaglandin $E_2$ Release by Leukocytic Pyrogen (Interleukin–1)," *N. Eng. J. Med.* 308(10):553–558 (1983).
Beutler B. and Cerami, A., "The Common Mediator of Shock, Cachexia, and Tumor Necrosis," *Adv. Immunol.* 42:213–231 (1988).
Beutler et al., "Passive Immunization Against Cachectin/Tumor Necrosis Factor Protects Mice from Lethal Effect of Endotoxin," *Science* 229:869–871 (1985).
Beutler et al., "Cachectin/Tumor Necrosis Factor: Production, Distribution, and Metabolic Fate in Vivo," *J. Immunol.* 135(6):3972–3977 (1985).
Black et al., "Chinese Hamster Ovarian Cells Transfected with the Murine Interleukin–6 Gene cause Hypercalcemia as well as Cachexia, Leukocytosis and Thrombocytosis in Tumor–Bearing Nude Mice," *Endocrinology* 128(5):2657–2659 (1991).
Breen et al., "Infection with HIV is Associated with Elevated IL–6 Levels and Production," *J. Immunol.* 144(2):480–484 (1990).
Candia et al., "Inhibition of HIV Replication and Cytopathicity in vitro by Synthetic Soluble Melanins," 6th Int'l Annual Conference on AIDS, p. Th. A. 228 XP002069206 (1990).
Cerami et al., "Weight Loss Associated with an Endotoxin–Induced Mediator from Peritoneal Macrophages: The Role of Cachectin (Tumor Necrosis Factor)," *Immunol. Lett.* 11:173–177 (1985).
Chantry et al., "Mechanism of immune complex–mediated damage: induction of interleukin 1 by immune complexes and synergy with interferon–γ and tumor necrosis factor–α," *Eur. J. Immunol.* 19:189–192 (1989).
Chiao et al., "α–Melanocyte–stimulating Hormone Reduces Endotoxin–induced Liver Inflammation," *J. Clin Invest.* 97(9):2038–2044 (1996).
Chomczynski, P. and Sacchi, N., "Single–Step Method of RNA Isolation by Acid Guanidinium Thiocyanate–Phenol–Chloroform Extraction," *Anal. Biochem.* 162:156–159 (1987).
Clark et al., "Possible Roles of Tumor Necrosis Factor in the Pathology of Malaria," *Am. J. Pathol.* 129(1):192–199 (1987).
Dayer et al., "Cachectin/Tumor Necrosis Factor Stimulates Collagenase and Prostaglandin $E_2$ Production by Human Synovial Cells and Dermal Fibroblasts," *J. Exp. Med.* 162:2163–2168 (1985).
Debing et al., "Melanosome Binding and Oxidation–Reduction Properties of Synthetic L–DOPA Melanin as In Vitro Tests for Drug Toxicity," *Mol. Pharmacol.* 33(4):470–476 XP002072899 (1988).
De Simone et al., "HIV–I infection and cellular metabolism," *Immunol. Today* 17(6):256–258 (1996).
Dewys et al., "Prognostic Effect of Weight Loss Prior to Chemotherapy in Cancer Patients," *Am. J. Med.* 69:491–497 (1980).
Drevlow et al., "Phase I Study of Recombinant Human Interleukin–1–Receptor (RHU IL–IR) Administered Subcutaneously in Patients with Active Rheumatoid Arthritis," *Arthritis Rheum.* 37:S339 Abstract 1070 (1994).
Duh et al., "Tumor necrosis factor α activates human immunodeficiency virus type 1 through induction of nuclear factor binding to the NF–κB sites in the long terminal repeat," *Proc. Natl. Acad. Sci. USA* 86:5974–5978 (1989).
Elliott et al., "Treatment of Rheumatoid Arthritis with Chimeric Monoclonal Antibodies to Tumor Necrosis Factor α," *Arthritis Rheum.* 36:1681–1690 (1993).

(List continued on next page.)

*Primary Examiner*—Theodore J. Criares
(74) *Attorney, Agent, or Firm*—Albert P. Halluin; Adam K. Whiting; Howrey Simon Arnold & White, LLP

(57) ABSTRACT

Methods and compositions are provided that teach the use of purified melanin compositions to treat, prevent, or ameliorate diseases that are associated with excess cytokine production. In particular, methods and compositions are provided that are useful in reducing the cellular production and release of the cytokine TNF-α, and the adverse disease consequences associated therewith.

9 Claims, 7 Drawing Sheets

OTHER PUBLICATIONS

Figure 1:
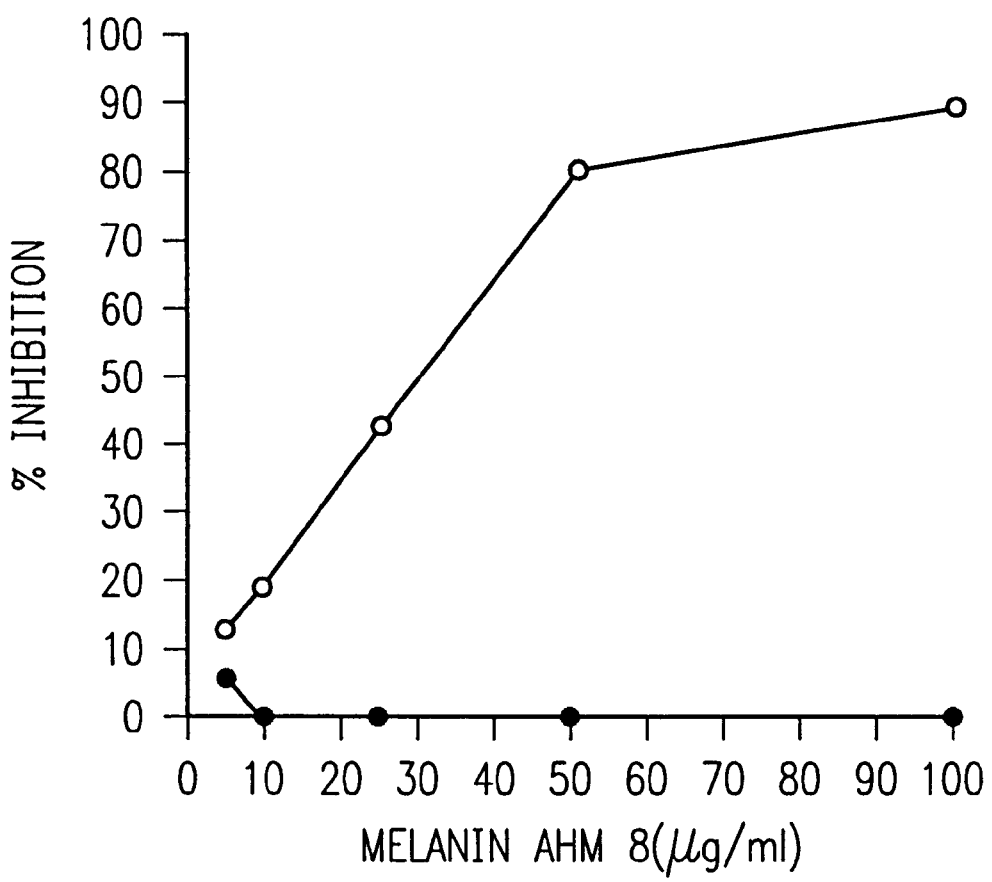
Figure 2A:
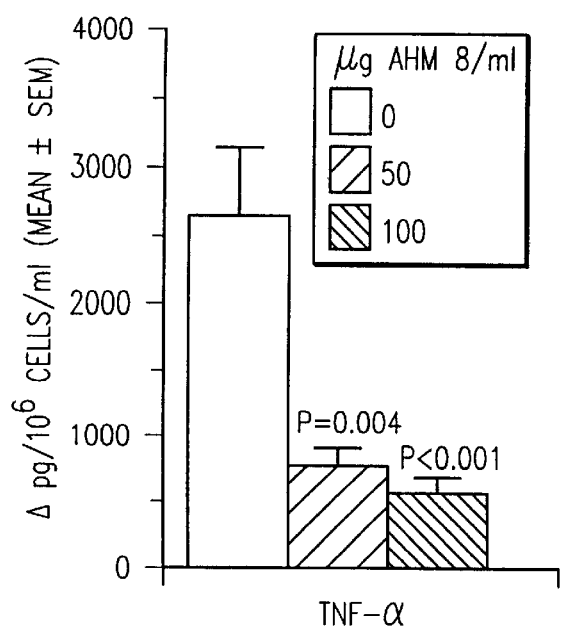
Figure 2B:
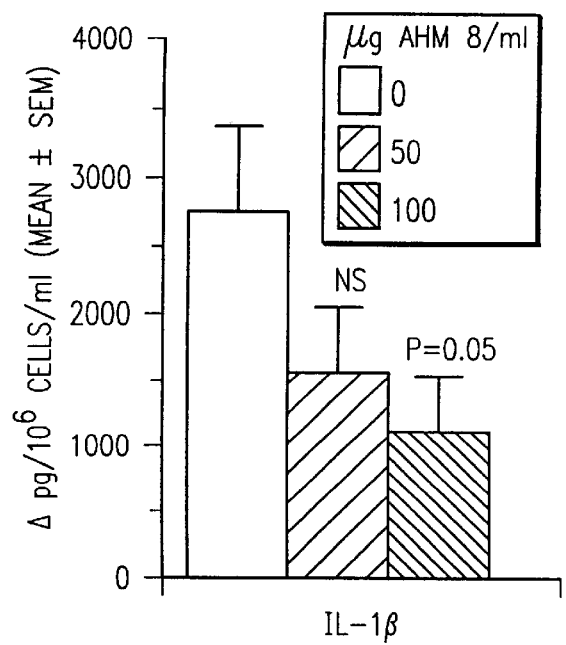
Figure 2C:
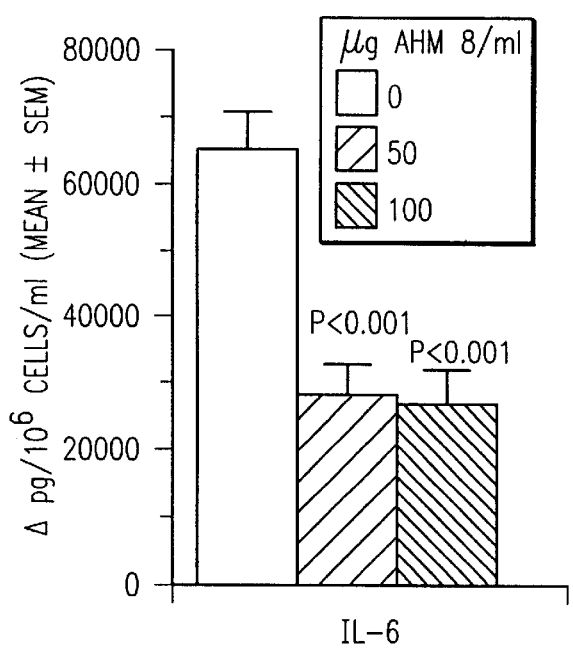
Figure 2D:
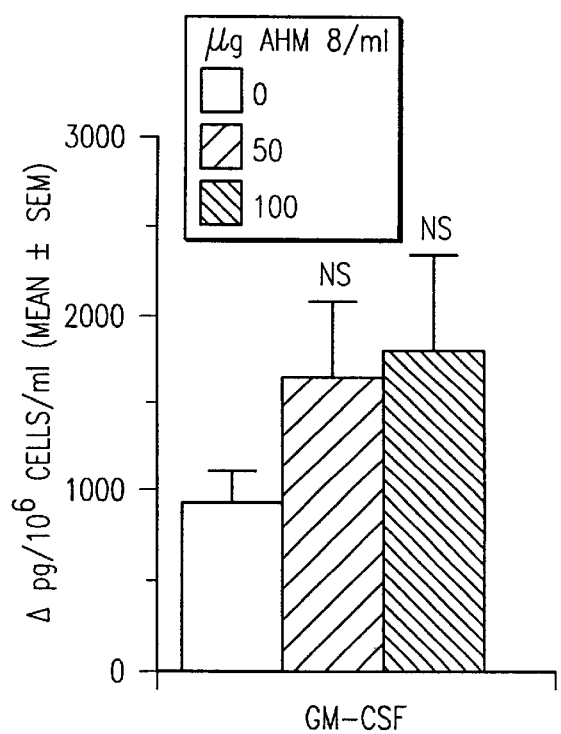

Elliott et al., "Randomised Double–blind Comparison of Chimeric Monoclonal Antibody to Tumour Necrosis Factor α (cA2) Versus Placebo in Rheumatoid Arthritis," *Lancet* 344:1105–1110 (1994).

Emilie et al., "Production of Interleukins in Human Immunodeficiency Virus–1–replicating Lymph Nodes," *J. Clin. Invest.* 86:148–159 (1990).

Feingold et al., "Effect of Tumor Necrosis Factor (TNF) on Lipid Metabolism in the Diabetic Rat," *J. Clin. Invest.* 83:1116–1121 (1989).

Feingold et al., "Tumor Necrosis Factor–Alpha Stimulates Hepatic Lipogenesis in the Rat In Vivo," *J. Clin. Invest.* 80:184–190 (1987).

Feingold et al., "Effect of Interleukin–1 on Lipid Metabolism in the Rat," *Arteriosclerosis Thromb.* 11(3):495–500 (1991).

Folks et al., "Cytokine–Induced Expresion of HIV–1 in a Chronically Infected Promonocyte Cell Line," *Science* 238:800–802 (1987).

Folks et al., "Tumor necrosis factor α induces expression of human immunodeficiency virus in a chronically infected T–cell clone," *Proc. Natl. Acad. Sci. USA* 86:2365–2368 (1989).

Fong et al., "Antibodies to Cachectin/Tumor Necrosis Factor Reduce Interleukin 1β and Interleukin 6 Appearance During Lethal Bacteremia," *J. Exp. Med.* 170:1627–1633 (1989).

Freudenberg et al., "Requirement for Lipopolysaccharide–Responsive Macrophages in Galactosamine–Induced Sensitization to Endotoxin," *Infect. Immun.* 51:891–895 (1986).

Gadina et al., "Protective Effect of Chlorpromazine on Endotoxin Toxicity and TNF Production in Glucocorticoid––Sensitive and Glucocorticoid–Resistant Models of Endotoxic Shock," *J. Exp. Med.* 173:1305–1310 (1991).

Gamble et al., "Stimulation of the adherence of neutrophils to umbilical vein endothelium by human recombinant tumor necrosis factor," *Proc. Natl. Acad. Sci. USA* 82:8667–8671 (1985).

Gange, R. and Jones, E., "Kaposi's Sarcoma and Immunosuppressive Therapy: an Appraisal," *Clin. Exp. Dermatol.* 3:135–145 (1978).

Grau et al., "Tumor Necrosis Factor (Cachectin) as an Essential Mediator in Murine Cerebral Malaria," *Science* 237:1210–1212 (1987).

Grau et al., "Tumor Necrosis Factor and Disease Severity in Children with Falciparum Malaria," *New England J. Med.* 320:1586–1591 (1989).

Greenfield et al., "Kaposi's Sarcoma in a Patient with SLE," *J. Rheumatol.* 13:637–640 (1986).

Grossman et al., "Interleukin 6 is Expressed in High Levels in Psoriatic Skin and Stimulates Proliferation of Cultured Human Keratinocytes," *Proc. Natl. Acad. Sci. USA* 86:6367–6371 (1989).

Grunfeld, et al., "Resting energy expenditure, caloric intake, and short–term weight change in human immunodeficiency virus infection and the acquired immunodeficiency syndrome[1–3]," *Am. J. Clin. Nutr.* 55:455–460 (1992).

Grunfeld et al., "Search for Mediators of the Lipogenic Effects of Tumor Necrosis Factor Potential Role for Interleukin 6," *Cancer Res.* 50:4233–4238 (1990).

Grunfeld C. and Feingold, K., "Metabolic Disturbances and Wasting in the Acquired Immunodeficiency Syndrome," *N. Eng. J. Med.* 327(5):329–337 (1992).

Guerne et al., "Synovium as a Source of Interleukin 6 In Vitro," *J. Clin. Invest.* 83:585–592 (1989).

Han et al., "Endotoxin–Responsive Sequences Control Cachectin/Tumor Necrosis Factor Biosynthesis At the Translational Level," *J. Exp. Med.* 171:465–475 (1990).

Hellerstein et al., "Interleukin–1–induced Anorexia in the Rat," *J. Clin. Invest.* 84:228–235 (1989).

Hirsch et al., "Complement Receptor–Mediated Uptake and Tumor Necrosis Factor–α–Mediated Growth Inhibition of *Mycobacterium tuberculosis* by Human Alveolar Macrophages," *J. Immunol.* 152:743–753 (1994).

Holler et al., "Increased Serum Levels of Tumor Necrosis Factor α Precede Major Complications of Bone Marrow Transplantation," *Blood* 75(4):1011–1016 (1990).

Horii et al., "Involvement of IL–6 in Mesangial Proliferative Glomerulonephritis," *J. Immunol.* 143:3949–3955 (1989).

Huffnagle et al., "Down–Regulation of the Afferent Phase of T Cell–Mediated Pulmonary Inflammation and Immunity by a High Melanin–Producing Strain of *Cryptococcus neoformans*," *Journal of Immunology* 155(7):3507–3516 XP002072897 (1995).

Jimbow et al., "Utilization of Melanin Precursors for Experimental Chemotherapy of Malignant Melanoma," *Japanese Journal of Cancer and Chemotherapy* 11(10):2125–2132 (1984) (Summary and references in English).

Kawano et al., "Autocrine Generation and Requirement of BSF–2/IL–6 for Human Multiple Myelomas," *Nature* 332:83–85 (1988).

Klausner et al., "The Effect of Thalidomide on the Pathogenesis of Human Immunodeficiency Virus Type 1 and *M. tuberculosis* Infection," *J. Acquir. Immun. Defic. Syndr. Hum. Retrovirol.* 11:247–257 (1996).

Kwiatkowski et al., "TNF concentration in fatal cerebral, non–fatal cerebral, and uncomplicated *Plasmodium falciparum* malaria," *Lancet* 336:1201–1204 (1990).

Lahdevirta et al., "Elevated Levels of Circulating Cachectin/ Tumor Necrosis Factor in Patients with Acquired Immunodeficiency Syndrome," *Am. J. Med.* 85:289–291 (1988).

Lawson et al., "Metabolic Approaches to Cancer Cachexia," *Ann. Rev. Nutr.* 2:277–301 (1982).

Lesslauer et al., "Recombinant Soluble Tumor Necrosis Factor Receptor Proteins Protect Mice From Lipopolysaccharide–induced Lethality," *Eur. J. Immunol.* 21:2883–2886 (1991).

Luce et al., "Ineffectiveness of High–dose Methylprednisolone in Preventing Parenchymal Lung Injury and Improving Mortality in Patients with Septic Shock," *Am. Rev. Respir. Dis.* 138:62–68 (1988).

Lupia et al., "Role of tumor necrosis factor–α and platelet–activating factor in neoangiogenesis induced by synovial fluids of patients with rheumatoid arthritis," *Eur. J. Immunol.* 26:1690–1694 (1996).

Markowicz, S. and Engleman, E., "Granulocyte–Macrophage Colony–stimulating Factor Promotes Differentiation and Survival of Human Peripheral Blood Dendritic Cells In Vitro," *J. Clin. Investig.* 85:955–961 (1990).

Marx, J., "Kaposi's Sarcoma Puzzle Begins to Yield," *Science* 248:442–443 (1990).

McGuire et al., "Variation in the TNF–α promoter region associated with susceptibility to cerebral malaria," *Nature* 371:508–511 (1994).

Michalek et al., "The Primary Role of Lymphoreticular Cells in the Mediation of Host Responses to Bacterial Endotoxim," *J. Infect. Dis.* 141:55–63 (1980).

Miles et al., "AIDS Kaposi sarcoma–derived cells produce and respond to interleukin 6," *Proc. Natl. Acad. Sci. USA* 87:4068–4072 (1990).

Millar et al., "Tumour Necrosis Factor in Bronchopulmonary Secretions of Patients with Adult Respiratory Distress Syndrome," *Lancet* 2:712–714 (1989).

Miossec, P., "The role of interleukin 1 in the pathogenesis of rheumatoid arthritis," *Clin. Exper. Rheumatol.* 5:305–308 (1987).

Mizel et al., "Stimulation of Rheumatoid Synovial Cell Collagenase and Prostaglandin Production by Partially Purified Lymphocyte–activating Factor (Interleukin 1)," *Proc. Natl. Acad. Sci. USA* 78(4):2474–2477 (1981).

Montefiori et al., "Inhibition of Human Immunodeficiency Virus Type 1 Replication and Cytopathicity by Synthetic Soluble Catecholamine Melanins In Vitro," *Biochemical and Biophysical Research Communications* 168(1):200–205 XP002069204 (1990).

Montefiori, D. and Zhou, J., "Selective antiviral activity of synthetic soluble L–tyrosine and L–dopa melanins against human immunodeficiency virus in vitro," *Antiviral Research* 15(1):11–26 (1991).

Moreland et al., "Soluble Tumor Necrosis Factor Receptor (sTNFR): Results of a Phase I Dose–Escalation Study in Patients With Rheumatoid Arthritis," *Arthritis Rheum.* 37:S295 (1994).

Munro et al., "Tumor Necrosis Factor and Interferon–γ Induce Distinct Patterns of Endothelial Activation and Associated Leukocyte Accumulation on Skin of *Papio anubis*," *Am. J. Pathol.* 135(1):121–133 (1989).

Nakajima et al., "Induction of IL–6 (B Cell Stimulatory Factor–2/IFN–$β_2$) Production by HIV," *J. Immunol.* 142(2):531–536 (1989).

Netea et al., "Pharmacologic Inhibitors of Tumor Necrosis Factor Production Exert Differential Effects in Lethal Endotoxemia and in Infection with Live Microorganisms in Mice," *J. Infect. Dis.* 171:393–399 (1995).

Offen et al., "Dopamine–Melanin Induces Apoptosis in PC12 Cells; Possible Implications for the Etiology of Parkinson's Disease," *Neurochem. Intl.* 31(2):207–216 (1997).

Ohlsson et al., "Interleukin–1 Receptor Antagonist Reduces Mortality from Endotoxin Shock," *Nature* 348:550–552 (1990).

Patton et al., "Development of Partial Tolerance to the Gastrointestinal Effects of High Doses of Recombinant Tumor Necrosis Factor–α in Rodents," *J. Clin. Invest.* 80:1587–1596 (1987).

Poli et al., "Interleukin 1 induces expression of the human immunodeficiency virus alone and in synergy with interleukin 6 in chronically infected U1 cells: Inhibition of inductive effects by the interleukin 1 receptor antagonist," *Proc. Natl. Acad. Sci. USA* 91:108–112 (1994).

Poli et al., "Interleukin 6 Induces Human Immunodeficiency Virus Expression in Infected Monocytic Cells Alone and in Synergy with Tumor Necrosis Factor α by Transcriptional and Post–transcriptional Mechanisms," *J. Exp. Med.* 172:151–158 (1990).

Raghavan et al., "Calculation of drug–melanin binding energy using molecular modeling," *Experentia* 46 (1):77–80 XP002072902 (1990).

Remington's Pharmaceutical Sciences, 15th edition, Mack Publishing Company, Easton, PA, pp. 1614–1615 (1975).

Rouzer, C. and Cerami, A., "Hypertriglyceridemia Associated with *Trypanosoma brucei brucei* Infection in Rabbits: Role of Defective Triglyceride Removal," *Mol. Biochem. Parisitol.* 2:31–38 (1980).

Saklatvala, J., "Tumour Necrosis factor α stimulates resorption and inhibits synthesis of proteoglycan in cartilage," *Nature* 322:547–549 (1986).

Sampaio et al., "Thalidomide Selectively Inhibits Tumor Necrosis Factor α Production by Stimulated Human Monocytes," *J. Exp. Med.* 173:699–703 (1991).

Saxne et al., "Detection of Tumor Necrosis Factor α But Not Tumor Necrosis Factor β in Rheumatoid Arthritis Synovial Fluid and Serum," *Arthritis Rheumatism* 31(8):1041–1132 (1988).

Shasby et al., "Endotoxin–induced pulmonary leukostasis," *Pathphysiolgy of Endotoxin*, L.B. Hinshaw, ed., Amsterdam: Elsevier Science Publishers, pp. 105–128 (1985).

Sidibe et al., "Effects of serotonin and melanin on in vitro HIV–1 infection," *J. Biol. Regul. Homeostatic Agents* 10(1):19–24 XP002069207 (1996).

Siegfried, C. and Hendricks, R., "Melanin can deplete immunosuppressive substances from the aqueous humor," *Current Eye Research* 13(12):869–873 XP002072900 (1994).

Spiegelman, B. and Hotamisligil, G., "Through Thick and Thin: Wasting, Obesity and TNFα," *Cell* 73:625–627 (1993).

Starnes et al., "Anti–IL–6 Monoclonal Antibodies Protect Against Lethal *Escherichia coli* Infection and Lethal Tumor Necrosis Factor–α Challenge in Mice," *J. Immunol.* 145(12):4185–4191 (1990).

Stein, C., "Suramin: A Novel Antineoplastic Agent with Multiple Potential Mechanisms of Action," *Cancer Res.* 53:2239–2248 (1993).

Strassmann et al., "Suramin Interferes with Interleukin–6 Receptor Binding In Vitro and Inhibits Colon–26–mediated Experimental Cancer Cachexia In Vivo," *J. Clin. Investig.* 92:2152–2159 (1993).

Tracey et al., "Anti–cachectin/TNF monoclonal antibodies prevent septic shock during lethal bacteraemia," *Nature* 330:662–664 (1987).

Vissers et al., "Glomerular Basement Membrane–Containing Immune Complexes Stimulate Tumor Necrosis Factor and Interleukin–1 Production by Human Monocytes," *Am. J. Pathol.* 134(1):1–6 (1989).

Waage et al., "Association between Tumour Necrosis Factor in Serum and Fatal Outcome in Patients with Meningococcal Disease," *Lancet* 8529:355–357 (1987).

Waleh et al., "Selective Down–Regulation of Integrin Receptors in Spheroids of Squamous Cell Carcinoma," *Cancer Res.* 54:838–843 (1994).

Wang, Y. and Casadevall, A., "Susceptibility of Melanized and Nonmelanized *Cryptococcus heoformans* to Nitrogen– and Oxygen–Derived Oxidants," *Infect. Immun.* 62:3004–3007 (1994).

Wendling et al., "Treatment of Severe Rheumatoid Arthritis by Anti–Interleukin 6 Monoclonal Antibody," *J. Rheumatol.* 20:259–262 (1993).

Wright et al., "Spontaneous Cytotoxicity and Tumor Necrosis Factor Production by Peripheral Blood Monocytes from Aids Patients," *J. Immunol.* 141:99–104 (1988).

Wright et al., "CD14, a Receptor for Complexes of Lipopolysaccharide (LPS) and LPS Binding Protein," *Science 249*:1431–1433 (1990).

Zhang et al., "Mechanisms of Stimulation of Interleukin–1β and Tumor Necrosis Factor–α by *Mycobacterium tuberculosis* Components," *J. Clin. Invest. 91*:2076–2083 (1993).

* cited by examiner

MEDIATION OF CYTOKINES BY MELANIN

1.0 FIELD OF THE INVENTION

Methods and compositions are described for the use of purified melanin to treat disease in animals and man. The disclosed melanin compositions are particularly useful for regulating cytokine production by mammalian and human cells both in vitro and in vivo.

2.0 BACKGROUND OF THE INVENTION

Tumor necrosis factor-alpha (TNF-α) is a 17-kd polypeptide released primarily by macrophages. Generally, TNF-α is not present in measurable quantity in sera from healthy individuals; but appears rapidly in response to immunostimulators (Beutler and Cerami, *Adv. Immunol.* 42:213–232, 1988). At physiological concentrations, TNF-α limits the growth and spread of invasive pathogens. However, excessive or uncontrolled production of this cytokine contributes to the pathogenesis of number of disease conditions.

TNF-α, acting alone and/or in concert with other mediators, evokes a potentially fatal syndrome of irreversible cardiovascular collapse (shock) and critical organ failure (Beutler, *Science* 229:869–871, 1985; Tracy et al., *Nature* 330:662–664, 1987; Waag et al., *Lancet* 1:355–357, 1987). Additionally, TNF-α acting in concert or in synergy with the interleukins IL-1 and IL-6 contributes to the development of wasting syndrome (cachexia) (Grunfeld, et al., *Am. J. Clin. Nutr.* 55:455–460, 1992; Grunfeld and Feingold, *N. Engl. J. Med.* 327:329–337, 1992).

For example, the experimental administration of supernatants from endotoxin-stimulated macrophages produced severe weight loss in rodents (Cerami et al., *Immunol. Lett.* 11:173–177, 1985). Moreover, nude mice implanted with genetically engineered tumor cells that secreted either TNF-α (Rouzer and Cerami, *Mol. Biochem. Parasitol.* 2:31–38, 1980) or IL-6 (Black et al., *Endocrinology* 128:2657–2659, 1991) became progressively anorectic and wasted. Administering TNF-α, IL-1, and IL-6 increases plasma triglycerides in rodents by boosting hepatic lipogenesis and very-low-density lipoprotein production leading to futile cycling of fatty acid/triglyceride and eventually wasting (Feingold and Grunfeld, *J. Clin. Invest.* 80:184–190, 1987; Grunfeld et al., *Cancer Res.* 50:4233–4238, 1990; Feingold, et al., *Arterioscler. Thromb. Vasc. Biol.* 11:495–500, 1991).

Cytokines also boost the levels of key catabolic hormones; alter glucose and amino acid metabolism; and have profound effect on food intake. In experimental animals, TNF-α decreases gastric motility and consequently leads to retention of food (Patten et al., *J. Clin. Invest.* 80:1587–1596, 1987), and IL-1 induces continuous anorexia by indirectly affecting the hypothalamic appetite center (Hellerstein et al., *J. Clin. Invest.* 84:228–235, 1989). In humans, wasting syndrome is often associated with cancer and a variety of infectious diseases including, but not limited to tuberculosis and AIDS.

In addition to progressive weight loss, many patients experience anorexia (reduced appetite), nausea, muscle weakness, and anemia (Lawson et al., *Lancet* 2:1–5, 1982; Grunfeld and Feingold, *New Engl. J. Med.* 237:329–337, 1992). Although cachexia may involve anorexia, usually the degree of lean body mass lost in cachexia associated with cancer and infectious disease cannot be explained by reduced caloric intake (Spiegelman and Hotamisligil, *Cell* 73:625–627, 1993).

Cachexia is considered as a detrimental end point because, apart from directly effecting patient survival, the progressive weight loss and anemia usually restrict the ability of cachectic patients to tolerate aggressive therapy (Dewy et al., *Am. J. Med.* 69:491–497, 1980).

The prevalence of cachexia makes this syndrome a significant medical problem. Taken together, these results provide a mechanistic basis for considering the use of melanin, an agent that interferes with the synthesis/release of IL-1, IL-6 and TNF-α, for managing wasting in patients.

TNF-α can also induce adult respiratory distress syndrome (ARDS), a severe consequence of gram-negative sepsis in humans (Shaby et al., In: *Pathophysiology of Endotoxin*, J. B. Hinshaw, ed. Amsterdam: Elsevier, pp. 105–128, 1985). TNF-α concentrations in excess of 12,000 pg/ml were detected in pulmonary aspirates from ARDS patients (Millar et al., *Lancet* 2:712–714, 1989). This cytokine is also known to increase the adherence of polymorphonuclear leukocytes to endothelial cells (Gamble et al., *Proc. Natl. Acad. Sci., U.S.A.* 82:8667–8671, 1985). Increased adherence of activated granulocytes in the microvasculature of the lungs and upper respiratory tract is one of the major causes of pulmonary vascular injury in ARDS. Of note, expression of intracellular adhesion molecule (ICAM), and endothelial leukocyte adhesion molecule (ELAM) on endothelial cells is either induced or enhanced by cytokines such as TNF-α or IL-1 (Munre et al., *Am. J. Pathol.* 135:121–132, 1989), a phenomenon which results in the augmentation of cell binding.

TNF-α, IL-1 and IL-6 also play a major role in the pathology of rheumatoid arthritis (Saklatvala., *Nature* 322:547–549, 1986; Miossec. *Clin. Rheumatol.* 5:305–308, 1987; Lupia et al. *Eur. J. Immunol.,* 26: 1690–1694, 1996). Synovial fluids from patients with rheumatoid arthritis contain TNF-α (Saxne et al., *Arthritis Rheumatism* 31:1041–1132, 1989) and IL-6 (Guerne et al., *J. Clin. Invest.* 83:585–592, 1989). Current evidence suggests that immune complexes may stimulate monocytes to secrete TNF-α (Visser et al., *Am. J. Pathol.* 134:1–6, 1989) and IL-1 (Chantry et al., *Eur. J. Immunol.* 19:189–192, 1989). TNF-α and IL-1 in turn stimulates production of proteases and prostaglandins by synoviocytes and bone resorption by osteoclasts (Miossec, *Clin. Rheumatol.* 5:305–308, 1987; Dayer et al., *J. Exp. Med.* 162:2163–2168, 1985; Saklatvala, *Nature* 322:547–549, 1986). Moreover, the presence of TNF-α and IL-1 in rheumatoid joints may act together to perpetuate synovitis by stimulating IL-6 synthesis which, if found in close proximity to plasma cells, may lead to autoantibody production. IL-6 is spontaneously produced by synoviocytes and high levels of IL-6 are present in synovial fluids from patients with inflammatory arthropathies (Guerne et al., *J. Clin. Invest.* 83:585–592, 1989).

Cerebral malaria is a lethal hyperacute neurological syndrome and prognosis of some malaria patients which has been associated with threshold levels of serum TNF-α (Grau et al., *Science* 237:1210–1212, 1987; Clark et al. *Am. J. Pathol.,* 129:192–199, 1987; Grau et al., *New Engl. J. Med* 320:1586–1591, 1989; Kwiatkowski et al., *Lancet* 336:1201–1204, 1990; McGuire et al. *Nature* 371–510, 1994). Similarly, in Graft versus Host Reactions, increases in TNF-α concentration have been associated with major complications (Holler et al., *Blood* 75:1011–1016, 1990).

TNF-α alone, or in synergy with either IL-1 or IL-6, enhances replication of HIV-1 in latently infected T cells and monocytes (Folks et al., *Science* 238:800–802, 1987; Folk et al., *Proc. Natl. Acad. Sci. U.S.A.* 86:2365–2368, 1989; Poli et al., *J. Exp. Med.* 172:151–158, 1990; Poli et al., *Proc. Natl. Acad. Sci. U.S.A.* 91:108–112, 1994). TNF-α is a strong inducer of NF-κβ, a transcriptional factor used by HIV (Nobel and Baltimore, *N. Engl. J. Med.* 234:308–317, 1987; Duh et al., *Proc. Natl. Acad. Sci. U.S.A.* 86:5974–5978, 1989). Moreover, synthesis of TNF-α, IL-1, and IL-6 are upregulated as a consequence of HIV infection (Folks et al., *Science* 238:800–802, 1987; Nakajima et al., *J. Inmunol.* 142:531–536, 1989). Serum and cerebrospinal fluid of patients with AIDS contain increased levels of TNF-α, IL-1, and IL-6 (Lahdevirta et al., *Am. J. Med.* 85:289–291, 1988; Emille et al., *J. Clin. Invest.* 86:148–159, 1990; Breen et al., *J. Immunol.* 144:480–484, 1990).

The apoptotic neuronal loss occurring in HIV-1 encephalitis is associated with TNF-α (DeSimone et al., *Immunol. Today* 17:256–258, 1996). In addition, TNF-α has been implicated in AIDS associated cachexia (Wright et al., *J. Immunol.* 141:99–104, 1988). Therefore, the downregulation of abnormal cytokine production by monocytes, and particularly the down-regulation of TNF-α is expected to retard the progression of HIV infection and provide supportive care for cachexic patients.

IL-6 is also an autocrine growth factor for cells derived from Kaposi sarcoma (KS) lesions of patients with AIDS (Miles et al., *Proc. Natl. Acad. Sci.* 87:4068–4072, 1990). KS, a multifocal vascular lesion, is also seen in other immunosuppressed states such as in patients receiving renal or cardiac transplants (Gang and Jones, *Clin. Exp. Dermatol.* 3:135–146, 1978; Greenfield et al., *J. Rheumatol.* 13:637–640, 1986). AIDS-KS-derived cell lines contain and secrete substantial amounts of IL-6 and AIDS-KS growth-enhancing effects of tat protein are mediated by increased IL-6 production. Indeed, addition of IL-6 antisense oligodeoxynucleotides to these cells resulted in decreased IL-6 production as well as marked inhibition of their growth (Miles et al., *Proc. Natl. Acad. Sci.* 87:4068–4072, 1990).

AIDS-KS derived cells produce other cytokines including IL-1 (Marx, *Science* 248:442–443, 1990) Addition of anti-IL-1 antibody to KS cell lines also resulted in decreased cellular proliferation. The increased levels of serum IL-6 and polyclonal B cell activation may be associated with increased frequency of B cell malignancies seen in AIDS patients (Akira and Kishimoto, *Immunol. Rev.* 127:26–50, 1992).

Like KS, the existence of an IL-6-IL-6-receptor autocrine loop has been implicated in the pathogenesis of multiple myeloma (Kawano et al., *Nature* 332:83–85, 1988). Elevated levels of IL-6 have been observed in other pathological conditions such as mesangial proliferative glomerulonephritis (Horii et al., *J. Immunol.* 143:3949–3955, 1989), and psoriasis (Grossman et al., *Proc. Natl. Acad. Sci.* 86:6367–6371, 1989).

A wide variety agents have been used to combat inflammation and life-threatening aspects of cytokines. Anti-TNF-α antibody, the TNF-α receptor, anti-IL-6, and IL-1 receptor antagonist (IL-1Ra) therapy were shown to reduce death after acute systemic toxicity (e.g., septic shock) in experimental animals (Beutler et al., *Science* 229:869–871, 1985; Tracy et al., *Nature* 330:662–664, 1987; Ohlsson et al., *Nature* 348:550–552, 1990; Starnes et al., *J. Immunol.* 145:4185–4191, 1990; Ashenazi, et al., *Proc. Natl. Acad. Sci. U.S.A.* 88:10535–10539, 1991; Lesslaner et al., *Eur. J. Immunol.* 21:2883–2886, 1991). However, the response to these cytokine blockers depended on the prophylactic administration of the agent, or the site of infection (Bagby et al., *J. Infect. Dis.* 163:83–88, 1991). Moreover, in a number of studies, anti-cytokine antibodies only partially protected the animals (Feingold et al., *J. Clin. Invest.* 83:1116–1121, 1989).

Data from several studies indicated that blockade of cytokines by infusion of either anti-TNF-α (Elliott et al., *Arthritis Rheum.* 36:1681–1690, 1993; Elliott et al., *Lancet* 344:1105–1110, 1994), or anti-IL-6 (Wendling et al., *J. Rheumatol.* 20:259–262) monoclonal antibody, as well as soluble TNF-α receptors (Moreland et al., *Arthritis Rheum.* 37:S295, 1994), or soluble IL-1 receptor (Drevlow et al., *Arthritis Rheum.* 37:S339, 1994) is effective in the treatment of rheumatoid arthritis. However, use of soluble cytokine receptors or antibodies to a single factor is constrained by the presence of multiple cytokines that participate in the manifestation of inflammatory conditions. Moreover, the large-scale treatment with anticytokine antibody may lead to production of anti-idiotypic antibodies.

Agents such as dexamethasone (Luce et al., *Am. Rev. Respir. Dis.* 138:62–68, 1988), pentoxifylline (Netea et al., *J. Infect. Dis.* 171:393–399, 1995), thalidomide (Klausner et al., *J. Acquir. Immun. Defic. Syndr. Hum. Retrovirol.* 11:247–257, 1996), suramin (Strassman et al., *J. Clin. Invest* 92:2152–2159, 1993), or α-melanocyte-stimulating hormone (α-MSH) (Chio et al., *J. Clin. Invest.* 97:2038–2044, 1996) have also been used for limiting synthesis of proinflammatory cytokines. With the exception of α-MSH, these agents have limited clinical utility because they are either ineffective when given after challenge (dexamethasone and pentoxifylline), do not target multiple cytokines, or have multiple side effects.

Thalidomide and pentoxifylline inhibit production of TNF-α but not IL-1β or IL-6 (Sampaio et al., *J. Exp. Med.* 173:699–703, 1991). Because multiple cytokines contribute to the pathogenesis of inflammatory disorders, inhibition of a single cytokine may not reverse or prevent the progression of disease. Thalidomide is teratogenic and has been used in the past as a sedative and antiemetic, and suramin has considerable toxicity (Stein, *Cancer Res.* 53:2239–2248, 1993).

Corticosteroids, the mainstay anti-inflammatory agents, manifest adverse effects such as susceptibility to infection, suppression of the hypothalamic-pituitary-adrenal axis, and Cushingoid features. Use of cyclosporine A may result in hypertension and nephrotoxicity.

Melanin, inter alia, is a free radical scavenger that acts as a bacterial virulence factor by protecting the organism from some host defense mechanisms (Wang and Casadevail, *Infect. Immun.* 62:3004, 1994). Additional studies have shown that melanin expression by bacteria may be a virulence factor that helps bacterial pathogens avoid the afferent phase of T cell-mediated immune responses in the host (Huffnagle et al., *J. Immunol.* 155:3507–3516, 1995).

3.0 SUMMARY OF THE INVENTION

The present invention is directed to the use of melanin as a therapeutic agent in animals, including humans. The preferred method of treatment comprises the administration of purified melanin, or biosynthetic melanin, to an animal in an amount sufficient to alleviate or prevent an adverse symptom of disease or illness. Accordingly, an object of the invention is a method of using purified melanin to treat or prevent illness in a patient which comprises administering melanin to the patient in an amount sufficient to provide a therapeutic benefit to the patient.

In a preferred embodiment of the present invention, the purified melanin provides a therapeutic benefit by being administered in an amount sufficient to modulate the immune response of the patient. In a particularly preferred embodiment, the purified melanin is administered in an amount sufficient to be associated with a decrease in host cytokine production, and in particular TNF-α, IL-1 and IL-6. In general, the decrease in cytokine production may be either a cause or effect of the beneficial clinical indications associated with the administration of purified melanins.

The purified melanins used in the presently described invention may also be administered in combination with a wide variety of pharmaceutically useful carriers or excipients. Accordingly, an additional embodiment of the present invention is the use of pharmaceutical compositions comprising purified melanin to reduce TNF-α production or otherwise provide a therapeutic benefit to a patient.

An additional embodiment of the present invention is the use of highly purified melanins that have a substantially homogeneous structure, and are substantially free of incorporated contaminating amino acids or derivatives thereof.

The presently described therapeutic use of purified melanin is particularly deemed to be useful for the treatment of cachexia, sepsis, acute respiratory distress syndrome, cerebral malaria, rheumatoid arthritis, epithelial ulcers of the skin and gut (particularly inflammatory bowel disease—ulcerative colitis, Crohn's disease, etc.), or other disorders associated with high levels of TNF-α or other cytokine expression or the adverse symptoms associated therewith.

In particular, given that graft rejection is often associated with an inflammatory response, an additional embodiment of the present invention is the use of purified melanin, or purified synthetic melanin, to reduce or prevent the rejection of transplanted organs and grafts. Similarly, the purified melanins are also deemed to be useful in the treatment and prevention of graft-versus-host disease.

In view of the above, an additional embodiment of the present invention is a method of modulating cytokine production by an animal cell by administering purified melanin to said cell in an amount sufficient to modulate cytokine production by said cell. In a preferred embodiment, the purified melanin will have been tested in vitro to verify that compositions comprising the purified melanin have the property of being capable of modulating cytokine expression by mammalian or other animal cells.

4.0. DESCRIPTION OF THE FIGURES

FIG. 1 shows that melanin inhibits LPS-induced TNF-α production. Open circles depict TNF-α production/release by monocytes (1×10$^6$ cells/ml) that were incubated for 40 min at 37° C. with various concentrations of melanin AHM 8 before stimulation with 1 ng/ml LPS. TNF-α production was measured in cell-free culture supernatants by ELISA. The TNF-α concentration was also determined for supernatants collected from monocytes stimulated with LPS in the absence of melanin (3,230 pg/10$^6$ cells/ml), and from supernatants collected from monocytes maintained in medium alone (36 pg/10$^6$ cells/ml).

Closed circles depict the effect of melanin on the constitutive synthesis of protein by melanin-treated cells. Monocytes (1×10$^5$ per 0.2 ml leucine-free medium supplemented with 10% dialyzed human AB serum) seeded in 96-well plates were incubated for 5 hr at 37° C. with the indicated concentrations of melanin AHM 8. Control cells were maintained in medium alone for the duration of culture. At 4 hours prior to harvest, cells were pulsed with 5 μCi per well of [$^3$H]-leucine. The mean (±SEM) incorporation of [$^3$H]-leucine by monocytes incubated in medium alone was 28,737±712 cpm.

FIGS. 2(A–D) show that melanin significantly inhibits production of TNF-α (FIG. 2A), IL-1β (FIG. 2B), and IL-6 (FIG. 2C), but not GM-CSF (FIG. 2D), by human peripheral blood monocytes. Monocytes were pretreated with the indicated concentrations of melanin AHM 8 (0 μg/ml, open bar; 50 μg/ml, slashed bar; 100 μg/ml, solid bar) before stimulation with 1 ng/ml LPS. Controls included (1) melanin-nontreated cells stimulated with LPS, (2) melanin-treated, LPS-nonstimulated monocytes, and (3) monocytes incubated in complete medium in the absence of additives.

The change (Δ) in the amount of pg of TNF-α=(pg cytokine/10$^6$ LPS-stimulated monocytes/ml)–(pg cytokine/10$^6$ LPS-nonstimulated monocytes/ml). The mean (±SEM) cytokine contents in the supernatant collected from 10$^6$ LPS-nonstimulated monocytes incubated in the presence of 0, 50, or 100 μg/ml melanin were, respectively, ≦108±5 pg/ml, for TNF-α; ≦75±53 pg/ml for IL-1β; ≦598±238 pg/ml for IL-6; and ≦168±124 pg/ml for GM-CSF.

Figure 3A:
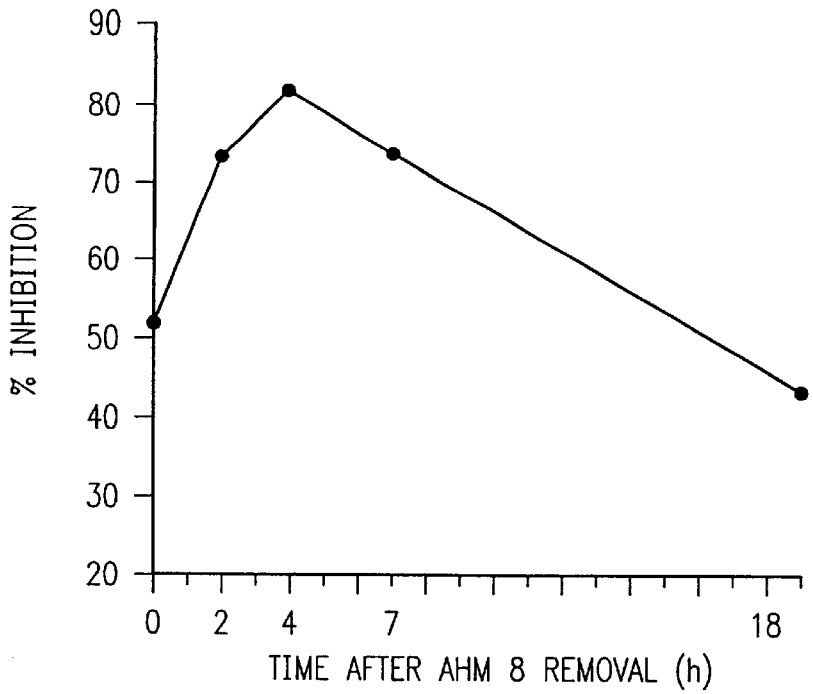
Figure 3B:
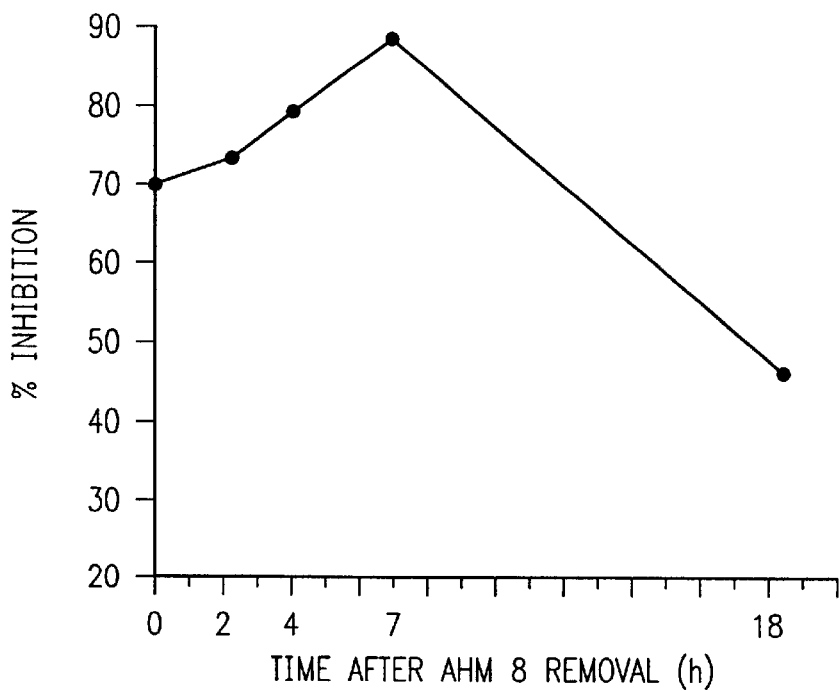

FIGS. 3(A & B) show duplicate experiments which indicate that the observed reversal of melanin-mediated suppression of TNF-α production is time-dependent. Human peripheral blood monocytes were incubated at 37° C. with 100 μg/ml melanin AHM 8. After a 1 hour incubation, cells were washed to remove free melanin, suspended in fresh medium, and stimulated with 1 ng/ml LPS at the indicated time points. The concentration of TNF-α in culture supernatants collected 24 hours after LPS addition was measured by ELISA, and the percent inhibition of TNF-α production is indicated.

Figure 4:
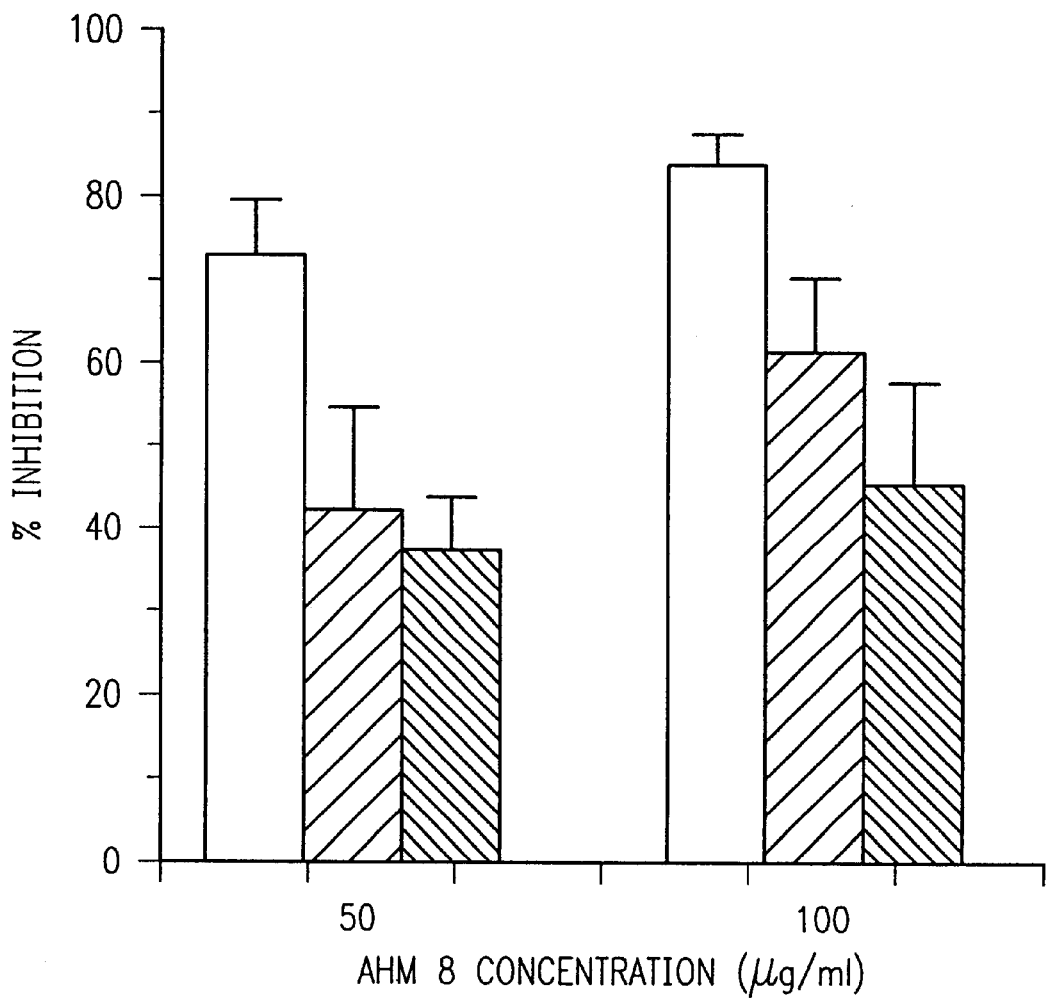
Figure 5A:
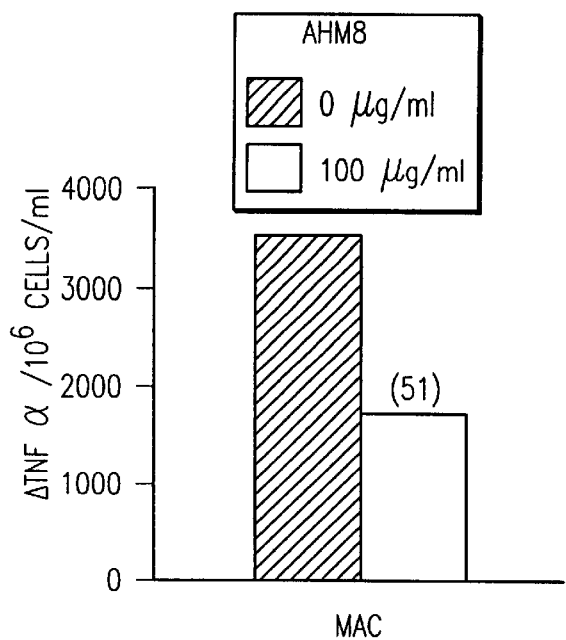
Figure 5B:
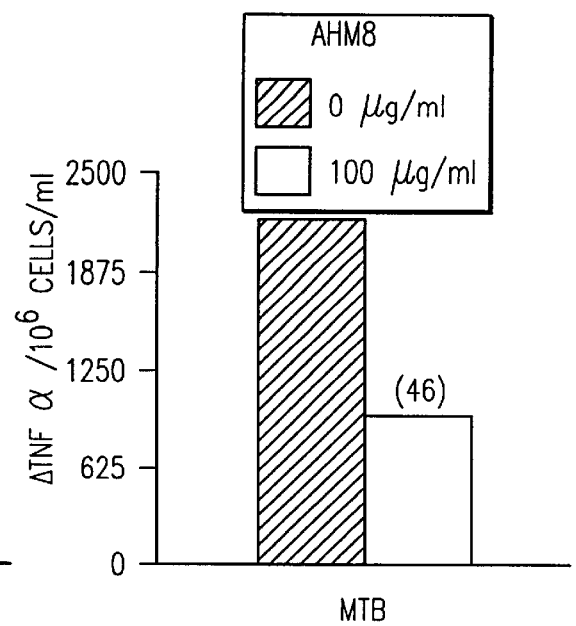
Figure 5C:
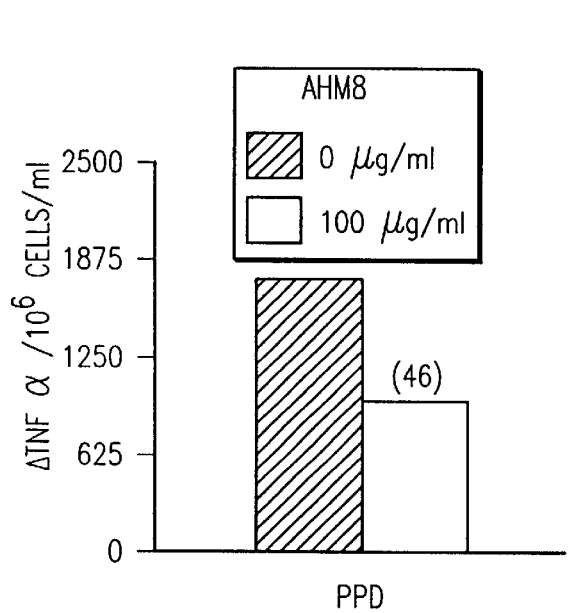
Figure 5D:
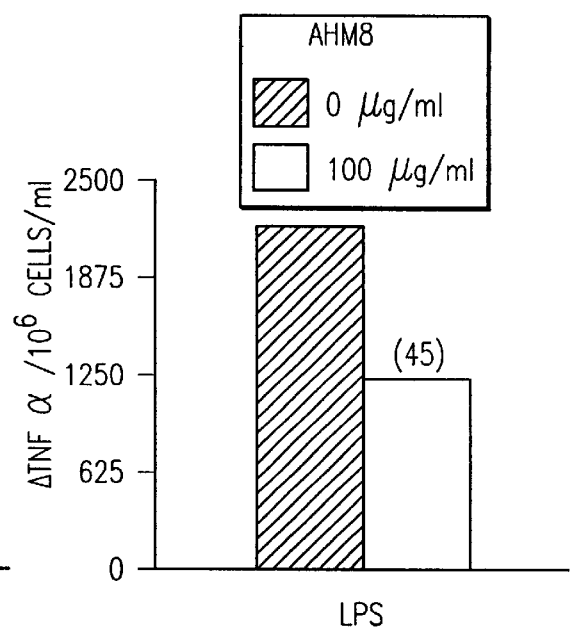

FIG. 4 shows that melanin treatment suppresses TNF-α production even when applied after LPS stimulation. Monocytes were stimulated with 1 ng/ml LPS either 1 hour after (open box), simultaneously with (slashed box), or 1 hour before (solid black box) the addition of the indicated amount of melanin (50 or 100 μg, respectively).

Control monocytes were incubated without LPS in either the absence or presence of melanin (not shown). Twenty-four hours after stimulation with LPS, the levels of TNF-α in the culture supernatants were measured by ELISA. At both concentrations, the amount TNF-α inhibition observed was greatest when the cells were pretreated with melanin, followed by cells simultaneously treated with melanin and LPS, and cells treated with after LPS stimulation (p<0.05 when compared to TNF-α production by monocytes treated for 1 hour with melanin before stimulation with LPS).

FIG. 5 (A–D) demonstrates that AHM 8 is able to inhibit TNF-α production independent of stimulus. Monocytes were infected with either *Mycobacterium avium* (MAC, FIG. 5A) strain 101 (serovar 1), or an avirulent (H37Ra) strain of *M. tuberculosis* (MTB, FIG. 5B) by incubation with an approximate bacterium:monocyte ratio of 10:1. Following a 4 hr incubation at 37° C., monocytes were thoroughly washed by low speed centrifugation to remove extracellular bacteria. Alternatively, monocytes were stimulated with either PPD (50 μg/ml, FIG. 5C) or LPS (1 ng/ml, FIG. 5D). After 24 hours of incubation in the presence of 100 μg/ml AHM 8, the release of TNF-α by monocytes infected with either MAC or MTB or stimulated with either PPD or LPS was reduced by 45–55%. The levels of TNF-α in each culture was measured by ELISA. The change (Δ) in the amount of pg of TNF-α/10$^6$ cells/ml=[pg of TNF-α/ml in the supernatant of AHM 8 treated and stimulated monocytes]–[pg of TNF-α/ml in the supernatant of AHM 8 treated and nonstimulated monocytes].

Figure 6:
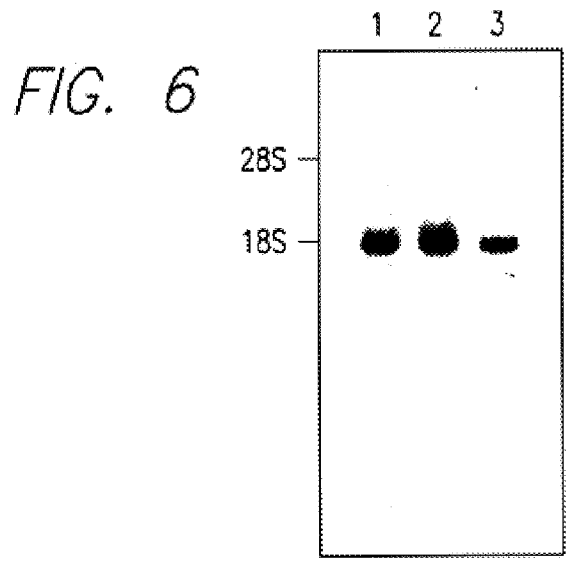

FIG. 6 shows the relative amount of TNF-α mRNA produced by human monocytes, cultured under nonadherent conditions, after treatment with either 0, 50 or 100 μg/ml AHM 8 for 1 hour before stimulation with 1 ng/ml LPS (lanes 1, 2, and 3, respectively). Total cellular RNA was extracted by the guanidinium thiocyanate method, size fractionated by formaldehyde/agarose gel electrophoresis (10 μg RNA/lane, normalized using a 28S RNA as a control), and transferred onto a nylon membrane by capillary blotting (Chomczynski and Sacchi, *Anal. Biochem.*, 162:156–159, 1987). The blot was hybridized to a 1.1 kb $^{32}$P-labeled cDNA fragment of TNF-α obtained by Pst I digestion of plasmid pE4 (American Type Culture Collection, Rockville, Md.). The data show that treatment with 100 μg/ml AHM 8 was able to reduce the amount of TNF-α mRNA produced by the cells (lane 3).

Figure 7A:
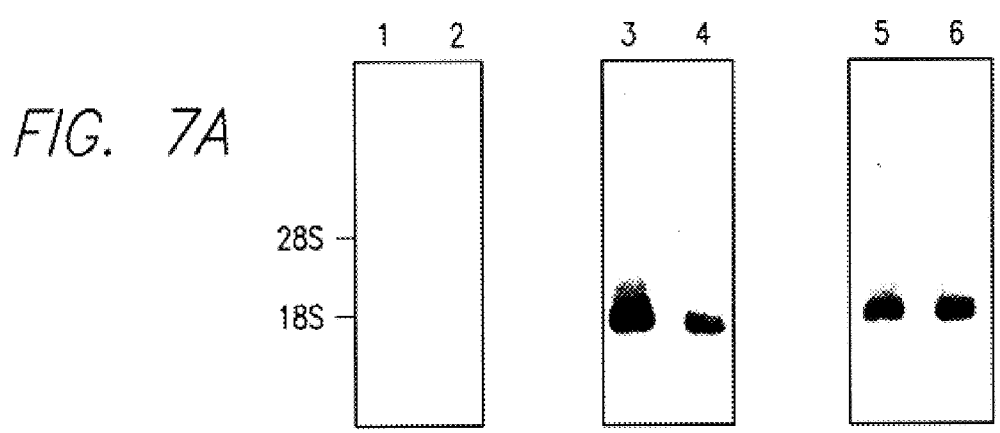
Figure 7B:
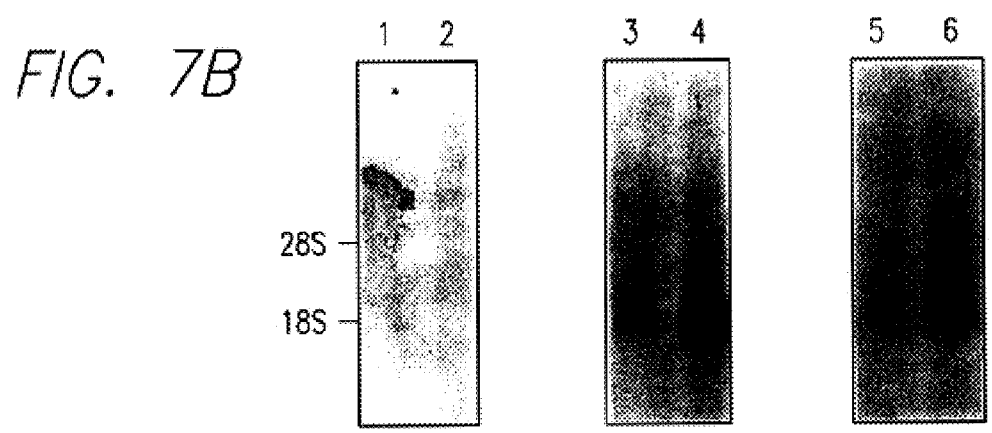

FIG. 7 shows a Northern blot that was performed using monocytes treated simultaneously with 1 ng/ml LPS and 100 μg/ml AHM 8. Control monocytes were stimulated with LPS in the absence of AHM 8. Total RNA, extracted 1 and 3 hours after LPS stimulation, was probed with cDNA fragment of human TNF-α (FIG. 7, Panel A) or IL-6 (FIG. 7, Panel B). Monocytes were incubated: for 1 hr in medium alone or in the presence of 100 μg/ml AHM 8 alone (lanes 1 and 2, respectively); for 2 or 3 hours in the presence of 1 ng/ml LPS alone (lanes 3 and 4, respectively); or for 2 or 3 hours in the presence of 1 ng/ml LPS and 100 μg/ml AHM 8 (lanes 5 and 6, respectively). Total cellular RNA was probed with $^{32}$P-labelled cDNA probes specific for TNF-α (panel A), or IL-6 (panel B) (using the 1.5 kb Bgl II/Bam HI fragment from pT7.7/hhIL-6 in *E. coli* BL21 (DE3), ATCC 68636).

Figure 8:
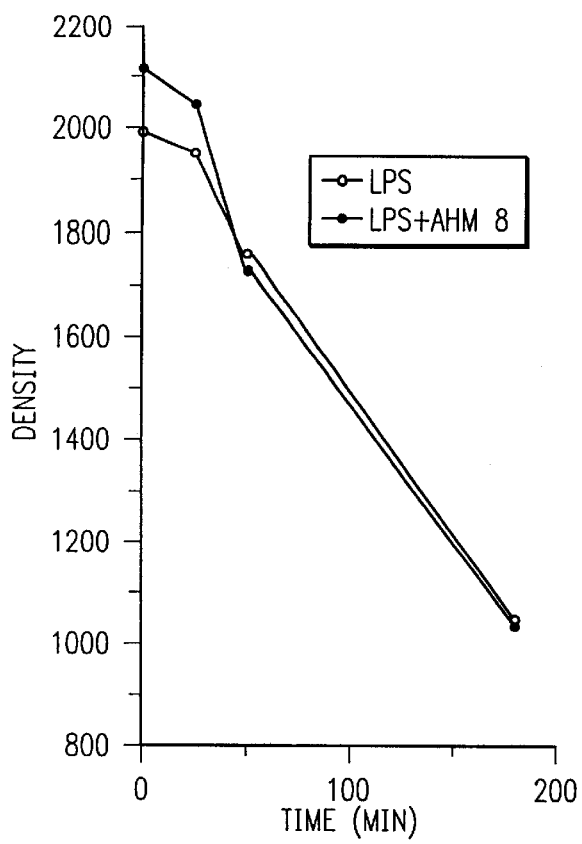

FIG. 8 shows that AHM-8 does not affect the stability of TNF-α mRNA. Monocytes were treated with 10 μg/ml actinomycin D 30 min after stimulation with 1 ng/ml LPS (time 0). A parallel culture of monocytes was simultaneously treated with actinomycin D and 100 μg/ml AHM 8. The decay of TNF-α mRNA was analyzed by Northern blot analysis 30, 60, and 180 min after addition of actinomycin D. Open and closed circles respectively represent cells cultured with LPS, or LPS and AHM 8.

FIGS. 9(A–C) shows that melanin strongly inhibits the TNF-α response in BALB/c mice. Circulating plasma concentrations of TNF-α were measured by ELISA 90 min after i.v. injection of LPS. AHM 8 (at 50 mg/kg, slashed bars) was injected either 60 min before (19 mice); simultaneously with (40 mice); or 15 min after (18 mice) LPS injection. The concentrations of TNF-α in the melanin treated group and nontreated controls (open bars) were compared by the two tailed Mann-Whitney Test using the INSTAT® 2.03 program. Results are mean ±SEM.

5.0. DETAILED DESCRIPTION OF THE INVENTION

The present invention is broadly directed to the discovery that melanin is useful for the therapeutic treatment of disease in animals, including humans.

In one embodiment, the melanins used in the presently described invention are substantially pure. In general, the term "substantially pure" melanin shall refer to melanin preparations that are comprised of at least about 75 percent of the desired melanin, specifically at least about 85 percent, more specifically at least about 90 percent, and preferably at least about 95 weight percent.

As a consequence of normal melanin production, a wide variety of protein and amino acid contaminants are typically incorporated into naturally occurring melanins. Additionally, the wide variety of substrates and contaminants that are typically available during normal melanin production in vivo may lead to the production of melanins with amorphous composition. Similarly, the wide variety of contaminants that are typically found in commercially available preparations of tyrosinase, the enzyme that makes melanin, are often incorporated into melanins produced in vitro.

Where pharmaceutical applications of melanin are contemplated, melanin products with defined and predictable compositions and structural features are highly desirable, and may even be necessary. Additionally, the contaminating proteins, and amino acids contained therein, that are often incorporated into naturally occurring or previously described melanins may also prove immunogenic in the host. Thus, melanin preparations that are to be administered in vivo shall preferably be substantially free of contaminating proteins, amino acids, and especially toxins of microbial origin (i.e., bacterial endotoxins, etc.).

The term "biosynthetic" melanin shall refer to melanin that is produced by a recombinantly expressed and/or purified tyrosinase protein that has been provided with a substrate for melanin production. By producing melanin using high specific activity tyrosinase in conjunction with defined substrates, melanins are produced with substantially more uniform structure and composition than melanins typically found in nature. With proper methods of synthesis, the resulting "biosynthetic" melanins may also be substantially pure, or further processed to produce biosynthetic melanin preparations that are substantially pure. In the majority of instances, suitably processed biosynthetic melanin may replace naturally occurring melanin in any of the embodiments described herein.

The purified or biosynthetic melanins used in the present invention may optionally be characterized by being substantially free of contaminating amino acid content. For the purposes of the present invention, the term "substantially amino acid free" shall refer to melanin preparations that generally contain less than about 10 percent amino acid content by weight, preferably less than about 7.5 percent amino acid content, more preferably less that about 5 percent amino acid content, and specifically less than 2.5 percent amino acid content by weight. Moreover, compositions comprising purified biosynthetic melanins shall generally be substantially free of potentially toxic contaminants of bacterial origin such as, but not limited to, bacterial endotoxins (particularly gram negative endotoxin), and bacterial exotoxins.

Where the therapeutic use of the presently described purified melanins is contemplated, the purified melanin is preferably administered in a pharmaceutically acceptable carrier, via oral, intranasal, rectal, topical, intraperitoneal, intravenous, intramuscular, subcutaneous, subdermal, transdermal, intrathecal, or intracranial methods, and the like. Typically, the preferred formulation for the purified melanin will vary depending upon the region of the host requiring treatment.

For example, topical immune reactions are preferably treated or prevented by melanin formulations designed for topical application, whereas systemic reactions are preferably treated or prevented by administration of compositions formulated for parenteral administration. Additionally, immune-mediated disorders of the pulmonary system may be treated both parenterally and by direct application of the therapeutic melanin compositions to the respiratory system by inhalation therapy. Additionally, local immune reactions, i.e., arthritic or inflamed joints, etc., may be treated by localized injection purified melanin compositions into the synovial capsule. Optionally, such local administration of purified melanin compositions may be performed in conjunction with corticosteroids.

Additionally, the purified melanin may be loaded into lipid-associated structures (i.e., liposomes, or other lipidic complexes) which may enhance the pharmaceutical characteristics of the purified melanin. The lipid-melanin complex may subsequently be targeted to specific target cells by the incorporation of suitable targeting agents (i.e., specific antibodies or receptors) into the melanin/lipid complex. Optionally, the purified melanin may be directly complexed with a targeting agent to produce the desired effect.

Where melanin mediated treatment of inflammatory disorders of the digestive tract and alimentary canal are contemplated, lipid formulations (e.g., emulsions, microemulsions, liposomes, etc.) comprising purified melanin may significantly protect the melanin from the digestive process. Accordingly, melanin formulations are contemplated that may be orally administered. To the extent that additional enteric protection is desired, for added protection, it is possible to formulate solid or liquid formulations in accordance with the invention in an enteric-coated or otherwise protected form. In the case of liquid formulations, they can either be mixed or simply coadministered with a protectant, such as a liquid mixture of medium chain triglycerides, or they can be filled into enteric capsules (for example of soft or hard gelatin, which are themselves optionally additionally enteric coated. Alternatively, solid formulations comprising melanin may be treated more flexibly. They may either be coated with enteric materials to form tablets or they can be filled into enteric capsules.

The thickness of enteric coating on tablets or capsules can be, for example, from 0.5 to 4 microns in thickness, although the precise thickness will be determined by the skilled formulator. Enteric coated granules (whose particle size may be, for example, from 0.5 to mm) may themselves be coated without being compounded into a tablet for coating. Microcapsules, similarly, can be enteric coated. The enteric coating may comprise any of the enteric materials conventionally utilized in orally administrable pharmaceutical formulations. Suitable enteric coating materials are known, for example, from "Remington's Pharmaceutical Sciences", 15th Edition, pp. 1614–1615 (1975); 2nd Edition, pp. 116–117, 371–374 (1976); and "Hagars Handbuch der Pharmazeutischen Praxie", 4th Edition, Volume 7a (Springer Verlag, pages 739 to 742 and 776 to 778 (1971).

Examples of suitable enteric coating materials include cellulose acetylphthalate, hydroxypropylmethylcellulosephthalate (HPMC-P), benzophenyl salicylate, cellulose acetosuccinate, copolymers of styrene and maleic acid, formulated gelatin, keratin, stearic acid, myristic acid, polyethylene glycol, shellac, gluten, acrylic and methacrylic resins and copolymers of maleic acid and phthalic acid derivatives. The enteric coating material(s) may be dissolved in solvents such as dichloromethane, ethanol and water, cellulose phthalate, or polyvinyl acetate phthalate. It is preferred to utilize HPMC-P, polyethylene glycol 6000 or shellac as the enteric coating. A proprietary preparation of HPMC-P aimed at dissolution or dissipation at pH 5.5, which is encountered in the human pylorus, is available under the trade mark HP5-5, and is particularly preferred.

Additionally, any of a variety of stabilizing agents may be utilized in conjunction with the described melanin compositions. Although the melanin itself may function as an antioxidant, the oxidation of melanin or other components of the described compositions may be substantially reduced by preparing formulations in accordance with the present invention under an inert atmosphere, such as nitrogen, this is a somewhat inconvenient and expensive process and so it is often preferred to add chemical anti-oxidants. Suitable pharmaceutically acceptable antioxidants include propyl gallate, butylated hydroxyanisole, butylated hydroxytoluene, ascorbic acid or sodium ascorbate, DL- or D-α-tocopherol and DL- or D-α-tocopheryl acetate. The anti-oxidant, if present, may be added singly or in combination to the polynucleotide delivery vehicles either before, during, or after vehicle assembly in an amount of up to, for example, 0.1% (w/v), preferably from 0.0001 to 0.05%.

Formulations comprising purified melanin may also be stabilized for storage and shipment by any of a number of well established methods, including but not limited to, freezing, refrigeration, and lyophilization. Where one seeks to augment long-term stability by freezing or freeze-drying melanin compositions, suitable excipients may be added to the melanin comprising preparations prior to freezing. Examples of such stabilizing excipients include, mono or disaccharides (e.g., glucose, sucrose, etc.), polysaccharides, or any of a variety of well-known agents (e.g., glycerols, gums, dextrans, and the like).

One of ordinary skill will appreciate that, from a medical practitioner's or patient's perspective, virtually any alleviation or prevention of an undesirable symptom (e.g., symptoms related to immune-mediated disorders in the body) would be desirable. Thus, the terms "treatment", "therapeutic use", or "medicinal use" used herein shall refer to any and all methods of using the described purified melanin compositions to remedy a disease state or symptoms, or otherwise prevent, hinder, retard, or reverse the progression of disease or any other undesirable symptoms in any way whatsoever. Similarly, a "therapeutically effective amount" of melanin is an amount sufficient to remedy a disease state or symptoms, or otherwise prevent, hinder, retard, or reverse the progression of disease or any other undesirable symptoms in any way whatsoever.

Given that adverse disease consequences have been linked with excess proinflammatory cytokines (i.e., TNF-α, and interleukins including, but not limited to, IL-1 and IL-6) production, in a particularly preferred embodiment of the present invention, the purified melanin is used at a dose that reduces or inhibits the excess production of TNF-α while still allowing or facilitating an effective host immune response against the underlying disorder or infection.

Preferably, animals that may be treated by the present invention include, but are not limited to, invertebrates, vertebrates, birds, mammals such as pigs, goats, sheep, cows, dogs, cats, and particularly humans.

When used in the therapeutic treatment of disease, an appropriate dosage of purified melanin, or modified form thereof, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Before human studies of efficacy are undertaken Phase I clinical studies in normal subjects help establish safe doses. Additionally, therapeutic dosages may also be altered depending upon factors such as the severity of infection, and the size or species of the host.

Particularly where in vivo use is contemplated, the various biochemical components used to formulate the present invention are preferably of high purity and are substantially free of potentially harmful contaminants (e.g., at least National Food (NF) grade, generally at least analytical grade, and preferably at least pharmaceutical grade). To the extent that a given compound must be synthesized prior to use, such synthesis or subsequent purification shall preferably result in a product that is substantially free of any potentially toxic agents, particularly endotoxins, which may have been used or present during the synthesis or purification procedures.

The presently described purified melanins may also be complexed with molecules that enhance their in vivo attributes. Examples of such molecules include, but are not limited to, carbohydrates, polyamines, amino acids, peptides, ions (i.e., sodium, potassium, calcium, magnesium, manganese, etc.), and lipids.

Additionally, the purified melanins may be complexed with a variety of well established compounds or structures that, for instance, further enhance the in vivo stability of the melanin, or otherwise enhance its pharmacological properties (e.g., increase in vivo half-life, reduce toxicity, enhance solubility or uptake, etc.). Examples of such modifications include, but are not limited to, the production of sulphate, gluconate, citrate, phosphate, and the like.

Where diagnostic, therapeutic or medicinal use of purified melanin, or derivatives thereof, is contemplated, the melanin may generally be prepared and maintained under sterile conditions that minimize that risk of, or avoid, microbial contamination. Because of the relatively small size and inherent stability of purified melanin, compositions comprising melanin may also be sterile filtered prior to use. In addition to the above methods of sterile preparation and filter sterilization, antimicrobial agents may also be added to the melanin compositions. Antimicrobial agents which may be used, generally in amounts of up to about 3% w/v, preferably from about 0.5 to 2.5%, of the total formulation, include, but are not limited to, methylparaben, ethylparaben, propylparaben, butylparaben, phenol, dehydroacetic acid, phenylethyl alcohol, sodium benzoate, sorbic acid, thymol, thimerosal, sodium dehydroacetate, benzyl alcohol, cresol, p-chloro-m-cresol, chlorobutanol, phenylmercuric acetate, phenylmercuric borate, phenylmercuric nitrate and benzylalkonium chloride. Preferably, antimicrobial additives will either enhance the biochemical properties of the melanin, or will be inert with respect melanin activity. To the extent that a given antimicrobial agent may prove deleterious to melanin activity, another agent may be substituted which effects the desired functions of melanin to a lesser extent.

One embodiment of the presently claimed methods relates to the use of purified melanin to modulate the immune system. Such modulation is deemed to be a function of melanin's ability to either directly or indirectly effect cytokine expression or activity in vivo or in vitro. In a preferred embodiment, the therapeutic use of melanin will downregulate cytokine expression. Melanin's ability to downregulate cytokine expression may also be exploited by using melanin in conjunction with established therapeutics in order to reduce the severity of the adverse immune-related reactions associated with a given therapeutic. For example, IL-2 treatment has been associated with adverse systemic consequences that are often dose dependent. Because of melanin's ability to modulate adverse immune reactions, the use of melanin in conjunction with cytokine may allow for the clinical use of higher systemic concentrations of cytokine. Accordingly, an additional embodiment of the present invention is the use of purified melanin to reduce the toxic side-effects of therapeutic agents.

Given that adverse disease consequences have been linked with excess TNF-α production, in a particularly preferred embodiment of the present invention, the purified melanin is used at a dose that reduces or inhibits the excess production of TNF-α while still allowing or facilitating an effective host immune response against the underlying disorder or infection.

For the purposes of the present invention, the term "cytokine" or grammatical equivalents thereof, shall generally refer to hormones that are associated with the cells of the immune system, both lymphokines and monokines, and others. The definition is meant to include, but is not limited to, those hormones that act locally and circulate in the blood, and which, when used in accord with the present invention, will result in an alteration of an individual's immune response. The term cytokine may refer to, but is not limited to, IL-1(α or β), IL-2, IL-3, IL-4, IL-5, IL-6, IL-7, IL-8, IL-9, IL-10, IL-11, IL-12, GM-CSF, M-CSF, G-CSF, LIF, LT, TGF-β, γ-IFN (or α or β-IFN), TNF-α, and BCGF. Descriptions of the aforementioned cytokines as well as other applicable immunomodulatory agents may be found in "Cytokines and Cytokine Receptors", A. S. Hamblin, 1993, (D. Male, ed., Oxford University Press, New York, N.Y.), or the "Guidebook to Cytokines and Their Receptors", 1995, N. A. Nicola, ed. (Oxford University Press, New York, N.Y.) herein incorporated by reference.

Given that melanin is useful for treating the wasting syndrome that is often associated with acquired immunodeficiency syndrome (AIDS), or cancer, the presently described methods are also deemed to be broadly useful for the treatment of AIDS and cancer.

An additional embodiment of the present invention is the use of purified melanin to treat allergy related hypersensitivity reactions. Particularly contemplated is the use of purified melanin to prophylactically treat individuals that may be susceptible to the adverse consequences of allergic reactions such as, but not limited to, drug reactions, insect stings, dermatitis, food allergies, and the like. Additionally contemplated is the intervening use of purified melanin to alleviate or reduce the adverse symptoms of allergic reactions.

Melanin is a virulence factor that contributes to the pathogenesis of a variety of infectious agents. To the extent that melanins that are characteristic of a particular pathogen may be identified, an additional aspect of the presently claimed invention is the use of purified melanin, or portions or analogues thereof, as vaccines to prevent progression and spread of melanin producing pathogens.

Similarly, the identification and use of melanoma associated or specific melanins is contemplated to provide an additional form of cancer therapy comprising the use of tumor specific melanins, or fragments or analogues thereof, as cancer vaccines, or tumor-specific immunostimulants.

Additionally, the identification of pathogen or tumor specific melanins shall be useful for the identification or production of receptors, ligands, or polyclonal or monoclonal antibodies that specifically bind to the pathogen or tumor specific melanin. Accordingly, an additional embodiment of the present invention are receptor, ligand, or antibody-based diagnostics or therapeutics that target pathogen or tumor specific melanins, or the cellular receptors therefore.

The following examples serve to more fully describe the manner of making and using the above-described invention, as well as to set forth the best modes contemplated for carrying out various aspects of the invention. It is understood that these examples in no way serve to limit the true scope of this invention, but rather are presented for illustrative purposes.

6.0. EXAMPLES

6.1. Synthesis of Water-Soluble Melanin

Water soluble melanin was produced and prepared for use essentially as described in U.S. Pat. Nos. 5,340,734; 5,466,592; 5,486,351; 5,210,076 and 5,057,325 herein incorporated by reference. Melanins produced using the described methods were further purified by acid precipitation by addition of concentrated HCl @pH 1.5. Precipitated melanin was recovered by centrifugation.

When analyzed for purity, the resulting melanin (designated AHM 8) was found to comprise about 96% percent of the final product by weight. The amino acid content of melanin AHM 8 was less than 4.2%. The total amino acid was 8.4% by weight of which 4.38% was tyr+gly. The elemental analysis yielded the following: % C=51.01; % H=3.74; % N=9.5; % S=0; and % O=33.85.

The endotoxin content of melanin AHM 8 was estimated using the chromogenic Limulus amebocyte lysate (CLAL) test kit (BioWhittaker, Inc., Walkersville, Md.). To determine whether AHM 8 has a direct inactivating effect on the CLAL test, in a preliminary experiment an aliquot of endotoxin standard containing 0.25 endotoxin unit (EU)/ml was spiked with 50 µg/ml AHM 8 (a dose similar to that used for treatment of monocytes). The endotoxin content of the "mixture" was determined using the CLAL test according to the manufacturer's directions. Percent reduction in the endotoxin content of melanin-containing standard preparation was calculated as follows:

% Inhibition={1-[(Endotoxin content of standard)-(Endotoxin content of AHM 8-containing standard)]/[Endotoxin content of standard]}×100

Results from this experiment indicated that AHM 8 does not markedly interfere with the CLAL assay. Addition of 50 µg/ml AHM 8 produced 22% reduction in the activity of the endotoxin standard. As shown in Table 1, the endotoxin content of melanin AHM 8, at 50 µg/ml, was only 0.069 endotoxin unit (EU)/ml. Under our experimental conditions, the production of TNF-α by human peripheral blood monocytes required 1.6 EU/ml of LPS (i.e., 0.1 ng LPS/ml).

TABLE 1

ENDOTOXIN CONTENT OF AHM 8

| Test Agent | Endotoxin Concentration (EU/ml) |
|---|---|
| PBS | 0 |
| LPS (0.05 ng/ml) | 1.50 |
| Mel AHM 8 (50 µg/ml) | 0.069 |

[a]Endotoxin content of each agent was estimated by CLAL test, using a commercially available kit.

When tested for the ability to induce TNF-α production, AHM 8 at 50 µg/ml did not induce a strong TNF-α response in human peripheral blood monocytes (123 pg TNF-α/$10^6$ cells/ml) (Table 2).

Peripheral blood monocytes used in this experiment, as well as those described in the following sections, were isolated from the white cell concentrates by sequential gradient centrifugation of Ficoll-Paque and Percoll gradient (Markowicz and Engleman, *J. Clin. Invest.* 85:955, 1990).

The white cell concentrates were purchased from Stanford University Blood Center (Palo Alto, Calif.). The percoll gradient consisted of sequential layers of 75%, 51.4%, 40%, and 30% dilutions of stock iso-osmotic solution of Percoll (1.128 g/ml) (Pharmacia Biotech, Uppsala, Sweden) in Dulbecco's calcium- and magnesium-free phosphate buffer saline (PBS) containing 5% heat-inactivated human serum. For further enrichment, low-density cells, mostly monocytes, were refloated onto a second Percoll gradient. The monocyte enriched population was resuspended at $1 \times 10^6$ cells/ml in macrophage serum-free medium (GIBCO, Grand Island, N.Y.) supplemented with 1% heat-inactivated human AB serum, 2 mM glutamine, 100 U/ml penicillin, and 100 µg/ml streptomycin [referred to hereafter as complete medium]. Because monocytes are stimulated to produce cytokine following adhesion to plastic, polypropylene tubes were used in these cell culture experiments.

TABLE 2

PRODUCTION OF TNF-α BY HUMAN PERIPHERAL BLOOD MONOCYTES INCUBATED IN THE PRESENCE OF MELANIN[a]

TNF-α Content of Culture Supernatants

| Cells Incubated with | (pg TNF-α/$10^6$ cells/ml) |
|---|---|
| Medium alone | 44 |
| AHM 8 (50 µg/ml) | 123 |
| LPS (0.1 ng/ml) | 1,013 |

[a]Monocytes were incubated with AHM 8 or LPS in polypropylene tubes. Following 24 h incubation at 37° C., culture supernatants were collected and TNF-α release was measured by ELISA (Biosource International, Camarillo, CA). Values are the mean of two measurements.

6.2. Pretreatment With Melanin Suppresses LPS-Induced TNF-α Production

The effect of biosynthetic melanin on in vitro TNF-α production was evaluated by comparing the levels TNF-α in the culture supernatants of melanin-treated and nontreated monocytes following stimulation with LPS. In these experiments, monocytes, ($1 \times 10^6$/ml), were incubated with various doses of melanin at 37° C. in a humidified atmosphere containing 5% $CO_2$. Following a 30–60 min incubation, monocytes were stimulated with LPS in the continuous presence of melanin. Controls included (1) melanin-nontreated cells stimulated with LPS; (2) melanin-treated, LPS-nonstimulated monocytes; and (3) monocytes incubated in complete medium in the absence of additives. Twenty-four hours after stimulation with LPS, the levels of TNF-α in the culture supernatants were measured, in duplicate, by ELISA (Biosource International, Camarillo, Calif.). The operable range for TNF-α was 15.6–1,000 pg/ml. Percent inhibition of the TNF-α response was calculated as follows:

% Inhibition=[1-(pg TNF-α/$10^6$ AHM 8-treated, LPS-stimulated monocytes)-(pg TNF-α/$10^6$ AHM 8-treated monocytes)/(pg TNF-α/$10^6$ AHM 8-nontreated, LPS-stimulated monocytes)-(pg TNF-α/$10^6$ monocytes maintained in medium alone)]×100.

As shown in FIG. 1, treatment of monocytes with melanin AHM 8 resulted in a dose-dependent inhibition of LPS-induced TNF-α production.

To ensure that the presence of melanin in the culture supernatants did not interfere with the assay (ELISA), the TNF-α concentrations in the supernatants collected from melanin-treated monocytes were determined from two standard curves. For construction of the "control standard curve", TNF-α standards were diluted in complete culture medium alone. "Melanin-containing standard curves" were constructed by plotting optical density (O.D.) values obtained from TNF-α standards (over a range from 0 to 1,000 pg/ml) that were diluted in complete medium incubated with 0–50 μg/ml melanin for 24 hours at 37° C. In parallel assays, the TNF-α content of culture supernatants collected from monocytes that were treated with 0–50 μg/ml melanin before stimulation with LPS (referred to hereafter as the test samples) were determined by reading their O.D. against each standard curve. The TNF-α content of each test sample, determined from different standard curves, was compared by calculating the Stimulation Index (SI) by dividing the amount (in pg) of TNF-α produced per $10^6$ cells per ml of supernatant from LPS-treated monocytes by the amount (in pg) of TNF-α produced per $10^6$ cells per ml of supernatant from non-LPS-treated monocytes.

As shown in Table 3, SI values of supernatants collected from melanin-pretreated monocytes were consistently lower than the SI values of supernatants collected from cells were not exposed to melanin. Taken together, these data indicate that melanin suppresses LPS-induced TNF-α synthesis/release by human monocytes and that this reduction is not the consequence of an inhibitory effect of melanin on the assay system.

TABLE 3

INFLUENCE OF MELANIN ON TNF-α-SPECIFIC ELISA[a]

| Melanin Content of TNF-α Standard (μg/ml) | TNF-α Content of Culture Supernatants from Cells Treated with AHM 8 (μg/ml) | | | |
|---|---|---|---|---|
| | 0 (Stimulation Index) | 10 | 25 | 50 |
| 0 | 78 | 39 | 17 | 7 |
| 10 | 69 | 35 | 16 | 7 |
| 25 | 82 | 40 | 17 | 7 |
| 50 | 75 | 37 | 17 | 7 |

[a]For construction of standard curves, complete medium containing 0 to 50 μg/ml AHM 8 was used to dilute TNF-α standards over a range from 0–1,000 pg/ml. The plate reader was zeroed against a blank composed of chromogen and stop solution.

6.3. The Effect of Melanin on Protein Synthesis by Human Peripheral Blood Monocytes To determine whether melanin selectively interferes with the production of LPS-induced cytokines, the effect of melanin AHM 8 on constitutive protein synthesis by human monocytes was measured. Protein synthesis was measured by incorporation of [$^3$H]leucine. Monocyte protein synthesis after 5 hours incubation in the presence of 100 μg/ml melanin AHM 8 was roughly comparable to that displayed by melanin nontreated control cells (23% lower). Under parallel experimental conditions incubation of monocytes with 20 μg/ml cycloheximide resulted in complete inhibition of [$^3$H]-leucine incorporation (1,219±51 cpm versus 28,737±712 cpm in control monocytes). In summary, even though pretreatment of monocytes with 100 μg/ml AHM 8 resulted in 90% suppression of TNF-α synthesis, net protein synthesis was only reduced by 23%.

The levels of [$^3$H]-leucine incorporation in monocytes incubated for 20 hours in the presence of 100 μg/ml AHM 8 was also comparable to that of the melanin nontreated cells (32,775±1,977 cpm versus 29,713±856 cpm).

6.4. Melanin Selectively Suppresses Cytokine Production by Human Monocytes

To determine whether melanin suppresses the production and release of other LPS-induced cytokines, peripheral blood monocytes were tested (essentially as described above) for the ability to produce TNF-α, IL-1β, IL-6 and granulocyte/macrophage-colony stimulating factor (GM-CSF) after melanin treatment. The levels of TNF-α, IL-1β, and GM-CSF in the culture supernatants were measured, in duplicate, using ELISA kits purchased from Biosource International (Camarillo, Calif.). ELISA kits used for measurement of IL-6 were purchased from R&D Systems (Minneapolis, Minn.). The operable range for the cytokines were TNF-α, 15.6–1,000 pg/ml; IL-1β, 3.9–250 pg/ml; IL-6, 3.12–300 pg/ml; and GM-CSF, 15.6–1,000 pg/ml. To ensure that the presence of AHM 8 in the culture supernatants did not interfere with the assay, the cytokine concentrations in the supernatants collected from AHM 8-treated monocytes were determined from standard curves that were constructed by plotting the O.D.'s obtained from the standards which were diluted in complete medium which had been incubated with 50 μg/ml AHM 8 for 24 hours at 37° C. The cytokine content of supernatants collected from AHM 8-nontreated monocytes' however, was determined from the "control standard curve". For construction of the "control standard curve", each standard was diluted in complete medium alone.

Results from these experiments are summarized in FIG. 2. Monocytes pretreated with AHM 8 produced significantly (p<0.05) lower levels of TNF-α, IL-1β, and IL-6 than did their respective controls. Under parallel conditions, melanin did not inhibit production or release of GM-CSF by LPS stimulated monocytes. In contrast, monocytes pretreated with 100 μg AHM 8/ml produced significantly higher levels of GM-CSF following stimulation with LPS (p<0.01). This indicates that AHM 8 does not inhibit LPS signalling. The finding that melanin does not suppress GM-CSF secretion is of particular interest. GM-CSF affects the intracellular phosphorylation of nucleoside analogues in monocytes and macrophages, resulting in increased activity of AZT and stavudine (De Simone et al., *Immunology Today* 17:256–258, 1996).

6.5. Continuous Presence of Melanin Is Not Required for Suppression of TNF-α Production To determine whether suppression of TNF-α production requires the continuous presence of melanin, freshly isolated human monocytes (1×$10^6$ cells/ml of complete medium) were treated with inhibitory concentrations of melanin AHM 8. Following a 1 hr incubation at 37° C., monocytes in one set of culture were stimulated with LPS in the continuous presence of melanin. Monocytes in a second set of cultures were washed once by low-speed centrifugation before stimulation with LPS. Controls included (1) melanin-nontreated cells stimulated with LPS; (2) melanin-treated, LPS-nonstimulated monocytes; and (3) monocytes incubated in complete medium in the absence of additives. Twenty-four hours after stimulation with LPS, the levels of TNF-α in the culture supernatants were measured in duplicate, by ELISA.

Suppression of TNF-α production did not require that melanin be continuously present. In fact, TNF-α production was suppressed by 63% even after the melanin had been washed out of the culture immediately before stimulation with LPS (data not shown).

6.6. Melanin-Mediated Suppression of TNF-α Production Is Reversible

To allow time for recovery, monocytes pretreated with the inhibitory concentrations of melanin AHM 8 were incubated for 2–18 hours in complete medium before stimulation with LPS. For each time point, the following cultures served as control: (1) melanin-nontreated, LPS-stimulated; (2)

melanin-nontreated, LPS-nonstimulated; and (3) melanin-treated, LPS-nonstimulated monocytes. The concentration of TNF-α in the culture supernatants was measured 24 hours after the addition of LPS.

Data from two experiments, shown in FIG. 3(A & B), demonstrate that melanin-mediated suppression of TNF-α persisted at least for 7 hours. The suppressive effects of melanin were reversed upon short-term culture. Monocytes stimulated with LPS 18 hours after removal of melanin exhibited a higher TNF-α response (44–47% decrease in TNF-α release versus a 74–88% reduction after a 7-hour AHM 8 washout period). These data indicate that monocytes treated with 100 μg melanin AHM 8/ml were not killed under these experimental conditions and that recovery from melanin-mediated suppression is time-dependent.

6.7. Melanin Suppresses Production of TNF-α by Activated Monocytes

The data presented in the preceding sections are from experiments in which monocytes were pretreated with melanin AHM 8 before LPS stimulation. To determine whether melanin suppresses production of TNF-α even when it is administered after LPS-stimulation, monocytes were treated with melanin either 1 hour after, simultaneously with, or 1 hour before stimulation with LPS. As expected, melanin added 1 hour before LPS drastically inhibited LPS-induced TNF-α production (84±4% inhibition at 100 μg/ml) (FIG. 4). When melanin was added 1 hour after LPS stimulation, a partial suppression of TNF-α response was observed (45±13% inhibition at 100 μg/ml, p=0.05). Melanin added at earlier time points following LPS stimulation did not exert a stronger suppressive effect. Treatment of monocytes with 100 μg/ml melanin either 7.5 or 60 min after LPS stimulation reduced TNF-α production by 50% and 52%, respectively (not shown). These data indicate that melanin may provide a corrective benefit as well as a preventative benefit, and may also indicate that at least two separate mechanisms are responsible for the net reduction in TNF-α production seen after prior exposure to melanin.

The finding that melanin appears less effective at suppressing TNF-α secretion by activated monocytes is of particular interest because this cytokine is an essential mediator in the immune response. This finding suggests that melanin could be used to reestablish a balanced or normal level of TNF-α in patients with wasting syndrome without destroying the patient's ability to fight infection.

6.8. Effect of Melanin on TNF-α Production Induced by Additional Stimuli

To test whether AHM 8 has the ability to modulate TNF-α production by cells that have been activated by stimuli other than LPS, additional stimuli are used in variations of the experiments outlined above with the exception that the dose of stimulating agent used is tailored as appropriate for the individual agent. Agents that are used in these assays include, but are not limited to, Mycobacterium, allergens (including compounds that have been associated with hypersensitivity reactions), and lectins.

To determine whether AHM 8 influences production of TNF-α by human monocytes regardless of stimulus, monocytes infected in vitro with *Mycobacterium avium* complex (MAC) [strain 101 (serovar 1)]; or an avirulent (H37Ra) strain of *M. tuberculosis* (MTB); or stimulated with the purified protein derivative of MTB (PPD) were treated with inhibitory concentrations of AHM 8. PPD, a known agonist of monocyte TNF-α synthesis and release, prepared from autoclaved culture filtrates of MTB was purchased from Connaught Laboratories Limited (Willowdale, Ontario, Canada). The results of these experiments, summarized in FIGS. 5(A–D), clearly demonstrate that the inhibitory effect of AHM 8 on TNF-α production/release is independent of stimulus. After 24 hours incubation in the presence of AHM 8, the release of TNF-α was reduced by 45–55% by monocytes infected with either MAC or MTB or stimulated with either PPD or LPS.

Unlike LPS, PPD does not stimulate TNF-α synthesis in monocytes through interaction with the cell surface protein CD14 (Wright, et al., *Science*, 249:1431–1433, 1990; Zhang et al., *J. Clin. Invest.* 91:2076–2083, 1993). The observed reduction in TNF-α production was not the consequence of diminished viability or higher bacterial burden of the AHM 8 treated monocytes. The exclusion of trypan blue was comparable for cells incubated with or without AHM 8 (93% vs 98%). In three experiments, 48±17% of monocytes incubated with 100 μg/ml AHM 8 contained acid fast bacilli as compared to 51±23% of the infected monocytes incubated in medium alone. The number of viable intracellular bacteria recovered from monocytes after 24 h incubation in the presence of 100 μg/ml AHM 8 was also similar to that yielded by monocytes maintained in medium alone (24±9 vs 24±4 colony forming MAC per cell, respectively, n=3).

To ensure that live mycobacteria as well as PPD, but not the contaminating LPS, stimulated production of TNF-α by monocytes, mycobacterial suspension or their product (PPD) were pretreated for 30 min with polymyxin B (PMB) before being added to the monocyte preparations. PMB inhibits LPS-induced cytokine production. As control, an aliquot of monocytes were incubated with LPS that had been preincubated with PMB. As expected, monocytes incubated with PMB-treated LPS failed to produce TNF-α (93% inhibition in cytokine release as compared to monocytes stimulated with PMB-nontreated LPS). In agreement with data from a previous study (Hirsch et al., *J. Immunol.* 152:743–753, 1994), preincubation with either MAC, MTB, or PPD with PMB had no effect on their TNF-α-inducing ability (data not shown).

6.9 Effect of melanin on the expression of TNF-α mRNA

Northern blot hybridization (Chomczynski and Sacchi, *Anal. Biochem.* 162:156–159, 1987; Waleh et al., *Cancer Res.* 54:838–843, 1994) was used to investigate the effect of AHM 8 on TNF-α mRNA expression in monocytes stimulated with LPS. Modulation of mRNA and protein levels occurs in tandem, however, this is not often the case. For example, increases in mRNA production may not translate into increase amounts of protein if the mRNA is unstable. Alternatively, translational interference or mRNA processing impediments may prevent a corresponding increase in protein production/release. TNF-α synthesis largely depends upon translational derepression (Han et al. *J. Exp. Med.* 171:465–475, 1990).

Initially, the effect of pretreatment with AHM 8 on accumulation of TNF-α mRNA by human monocytes was examined. Human monocytes, cultured under nonadherent conditions, were treated with either 0, 50 or 100 μg/ml AHM 8 for 1 hour before stimulation with 1 ng/ml LPS (lanes 1, 2, and 3, respectively, in FIG. 6). Pretreatment of monocytes with the indicated noncytotoxic doses of AHM 8 results in strong (66–83%) inhibition of LPS-induced TNF-α production/release (see FIG. 1). One hour after LPS stimulation, monocytes were collected and lysed for mRNA expression studies. Data from previous studies (not shown) indicated that in monocytes TNF-α mRNA expression peaks within 1 hour of LPS stimulation and declined thereafter.

As shown in FIG. 6, AHM 8 at 50 μg/ml had no inhibitory effect on the LPS-induced TNF-α mRNA expression (compare lanes 1 and 2). However, TNF-α mRNA expression decreased in response to 100 μg/ml AHM 8 (compare lanes 1 and 3). The level of mRNA, assessed by using a video densitometer, was 26% lower than that expressed by monocytes stimulated with LPS in the absence of AHM 8.

In subsequent studies, Northern blot analysis was performed using monocytes treated simultaneously with 1 ng/ml LPS and 100 μg/ml AHM 8. Control monocytes were stimulated with LPS in the absence of AHM 8. Monocytes incubated either in medium alone or in the presence of 100 μg/ml AHM 8 served as additional controls. Total RNA, extracted 1 and 3 hours after LPS stimulation, was probed with cDNA fragment of human TNF-α (FIG. 7, Panel A) or IL-6 (FIG. 7, Panel B). For determination of TNF-α release, monocytes in the second set of cultures were incubated at 37° C. for 24 hours. The levels of TNF-α in the culture supernatants were measured by ELISA.

As shown, when added simultaneously with LPS, AHM 8 diminished the accumulation of TNF-α as well as IL-6 mRNA. In this experiment, mRNA levels for both cytokines were depressed by 25%; TNF-α synthesis/secretion was, however, reduced by 68%. AHM 8 alone had no stimulatory on TNF-α mRNA expression (lane 2); the amount of mRNA present in AHM 8 treated cells was comparable to that of the background (cells maintained in medium alone) (lane 1).

To rule out the possibility that AHM 8 affects TNF-α mRNA stability, degradation of mRNA in the LPS-stimulated monocytes was evaluated in the presence of 10 μg/ml actinomycin D. As depicted in FIG. 8, TNF-α mRNA extracted from the LPS-stimulated monocytes treated with either a combination of actinomycin D and 100 μg/ml AHM 8 or actinomycin D alone have similar degradation profiles, indicating that AHM 8 does not affect TNF-α mRNA stability.

Taken together, these findings indicate that AHM 8 achieves its regulatory effects through different mechanisms. At 100 μg/ml, AHM 8 modestly inhibits TNF-α gene transcription, but exerts a strong inhibitory effect on translational or processing events even at 50 μg/ml.

6.10. Effect of Melanin on TNF-α Production In Vivo

To determine whether melanin reduces cytokine production in vivo, circulating concentrations of TNF-α were measured in mice that had been injected with AHM 8 either before or, concomitantly with, or after challenge with LPS. The release of proinflammatory cytokines, including TNF-α, triggers multiple cellular and molecular events including the expression of adhesion molecules (including intercellular adhesion molecules-1 and E-selectin), and the production of secondary inflammatory mediators (e.g., prostaglandins) in the course of inflammatory disease (Mizel et al., *Proc. Natl. Acad. Sci. U.S.A.* 78:2474–2477, 1981; Dayer et al., *J. Exp. Med.* 162:2163–2168, 1985). Prostaglandin stimulates the production of intracellular proteases (Baracos et al., *N. Engl. J. Med.* 308:553–555, 1983). TNF-α is one of the earliest factors produced during acute inflammation (i.e., endotoxemia) (Michalek, et al., *J. Infect. Dis.* 141:55–63, 1980; Beutler et al., *J. Immunol.* 135:3972–3977, 1985; Freudenberg et al., *Infect. Immun.* 51:891–895, 1986; and Fong et al., *J. Exp. Med.* 170:1627–1633) and the level of this cytokine is a predictive indicator of the outcome in endotoxin shock (Waage et al., *Lancet* 8529:355–357, 1987). Therefore, the in vivo TNF-α response to LPS was used as a model to determine the cytokine regulatory effects of melanin.

In these studies, female BALB/c mice were injected intravenously (i.v.) with a previously determined dose of LPS (0.625 mg/Kg) and 50 mg AHM 8/Kg body weight (Acute toxicity studies showed that a single i.v. dose of 5 g/kg melanin was well tolerated by Sprague Dawley rats). Control mice received either LPS, AHM 8, or PBS. A PBS sham injection was given to each mouse in the control group to balance the total number of injections as well as the i.v. fluid load of 10 ml/kg. After 90 min, blood was collected in 0.5 ml tubes containing 0.750 μg EDTA (Microtainer tubes #5973; Becton Dickinson) and 50 μg aprotinin (Sigma Chemical Co). Plasma was separated within 3–5 min of blood collection by centrifugation at 4° C. and stored at −70° C. for ≦7 days until assayed. Each plasma sample was thawed once. Preliminary time course studies showed that in BALB/c mice, the peak TNF-α response occurred 90 min after LPS administration. The TNF-α content of each plasma sample was measured, in duplicate, by ELISA (BioSource International). A minimum of 10 mice were included in each group because (1) normal mice exhibit varying sensitivity to endotoxin, and therefore there is a high degree of variability in their TNF-α response; (2) TNF-α has a short half-life in plasma (approximately 6–7 min in mice) (Beutler et al., *J. Immunol.* 135:3972–3977, 1985); and (3) soluble TNF-α receptors interfere with cytokine measurements (Aderka et al., *Cancer Res.* 51:5602–5607, 1991). For confirmation, each experiment was repeated 2–4 times.

Figure 9A:
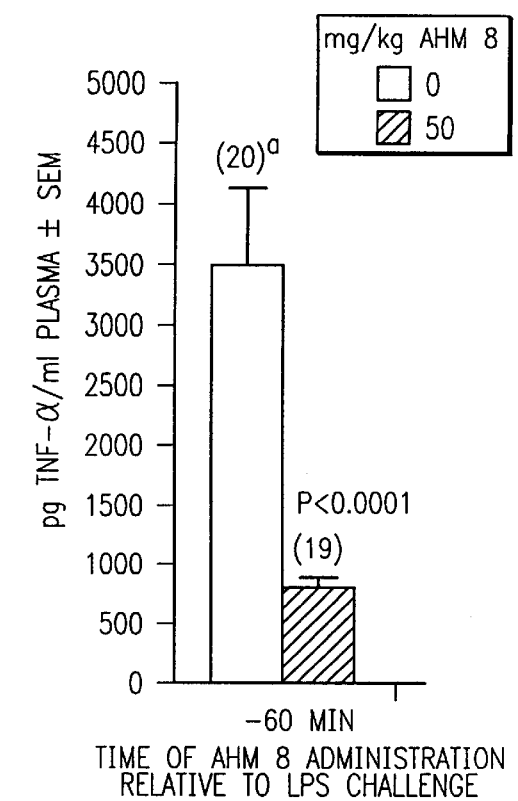

Results from two subsequent experiments showed that plasma TNF-α levels in mice injected with 50 mg/kg melanin 60 min before challenge with LPS was 77% lower than those injected with LPS alone (FIG. 9A, p<0.001). The concentration of TNF-α in the plasma of 10 mice given either melanin alone or PBS (the vehicle) was 33±16 and 45±17 pg/ml, respectively.

Figure 9B:
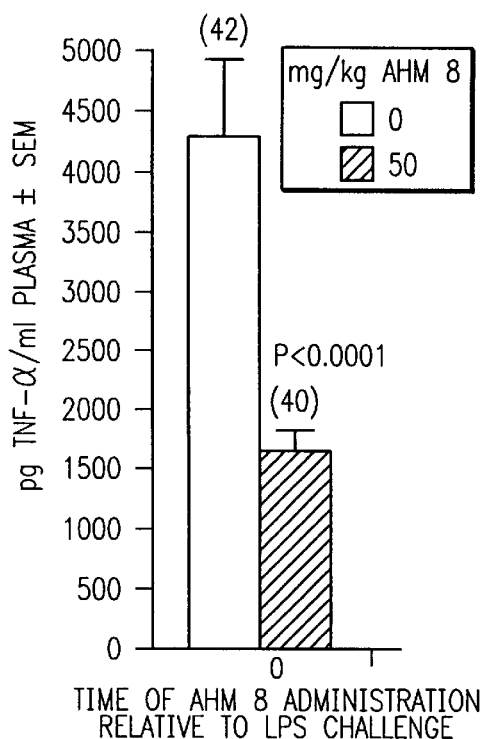

The LPS-stimulated increase in TNF-α production/release reduced by 62% (n=40) when mice were injected concomitantly with LPS and 50 mg/Kg AHM 8 (FIG. 9B, p<0.0001). Melanin was also inhibitory at 25 mg/Kg. The plasma TNF-α concentration in 12 mice injected concomitantly with 0.625 mg/Kg LPS and 25 mg/kg AHM 8 was 62% lower than in animals injected with LPS alone (1,702±345 pg/ml vs. 4,473±1,913 pg/ml, p=0.05). The inhibitory effect exerted by AHM 8 was not due to direct interaction of melanin with LPS because in these experiments mice were first injected in one tail vein with LPS and immediately into a second tail vein with AHM 8.

Figure 9C:
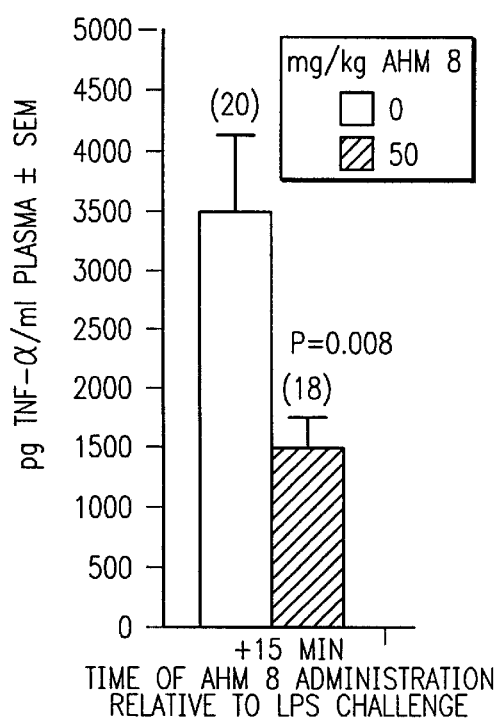

Melanin was also effective when administered 15 min after LPS challenge. As shown in FIG. 9C, the levels of circulating TNF-α in mice injected with melanin 15 min after LPS administration was significantly (p=0.008) lower than the corresponding controls injected with LPS alone. However, melanin was incapable of down regulating TNF-α production/release when injected 30 min after LPS insult (data not shown). These results are consistent with the relatively transient (60–90 min) peak of circulating TNF-α in mice (Garina et al. *J. Exp. Med.* 173:1305–1310, 1991), and suggest that once the posttranscriptional phase of TNF-α biosynthesis has been completed, melanin is incapable of downregulating the process.

Taken together these data indicate that melanin significantly reduces TNF-α production/release under acute inflammatory condition and that there is no need for pretreating the animals to achieve the protective effect of melanin.

Although mice have been specifically exemplified in the above in vivo studies, typically, any acceptable animal model may be used to assess purified melanin's ability to modulate cytokine expression in vivo. Additionally, experimental protocols and conditions will necessarily be adjusted as applicable depending on the mitogen to be tested, and the mode of injection. Accordingly, the following disclosure provides an example of an in vivo study where prior treatment with melanin provides prophylactic protection against subsequent challenge with endotoxin. The following example is provided solely for purposes of exemplification and should not be deemed as limiting the present invention in any way whatsoever.

Typical animal tests comprise a minimum of about 5–8 animals in each treatment group in order to adequately demonstrate the statistical reproducibility of a given experimental observation. By using at least about 10 test animals, one can compensate for variabilities such as differing sensitivity of microorganisms in a given animal and any variables introduced by the repeated handling and injection of the animals.

Purified melanin (AHM 8) is usually injected i.v. and is generally introduced into test animals at a concentrations of between about 10 and about 200 mg/kg body weight, and preferably between about 25 and about 75 mg/kg body weight, and specifically at about 50 mg/kg body weight. Control subjects are injected with corresponding volumes of buffered saline.

Following melanin treatment, the various control and test subjects are injected with a variety of sub-lethal and lethal doses of mitogen (LPS, or other agents useful for simulating the symptoms of systemic sepsis or shock). Blood samples are drawn at suitable time intervals after introduction in order to quantify the amounts of purified melanin and cytokine that are present in the bloodstream. Alternatively, where lethal doses of mitogen are used, the extent to which melanin confers protection to the test animals is determined.

It will be understood by those skilled in the art that various modifications of the present invention as described in the foregoing examples may be employed without departing from the scope of the invention. Many variations and modifications thereof will be apparent to those skilled in the art and can be made without departing from the spirit and scope of the invention herein described. All patents and publications referenced herein are hereby incorporated by reference in their entirety.

I claim:

1. A method of modulating cytokine production by an animal, comprising administering purified melanin to said animal in an amount sufficient to alleviate or reduce an adverse symptom of a disease associated with cytokine expression wherein said disease is drawn from the group consisting of cachexia, arthritis, tendinitis, inflammatory bowel disease, sepsis, shock, and allergy.

2. A method according to claim 1 wherein said disease is cachexia.

3. A method according to claim 1 wherein said disease is arthritis.

4. A method according to claim 1 wherein said disease is inflammatory bowel disease.

5. A method according to claim 1 wherein said disease is allergy.

6. A method of reducing the systemic toxicity of a therapeutic agent for a non-neurodegenerative disease comprising administering purified melanin to an individual in an amount sufficient to reduce or alleviate an adverse symptom associated with said therapeutic agent.

7. The method of claim 6 wherein the disease is drawn from the group consisting of cachexia, arthritis, tendinitis, inflammatory bowel disease, sepsis, shock, and allergy.

8. A method according to claim 6 wherein said disease is graft rejection.

9. A method according to claim 6 where in said disease is graft versus host disease.

* * * * *